United States Patent
Charmley et al.

(10) Patent No.: US 7,879,982 B2
(45) Date of Patent: *Feb. 1, 2011

(54) 19.5 POLYPEPTIDE ANTIBODIES USEFUL FOR DIAGNOSING OR TREATING PSORIASIS

(75) Inventors: Patrick R. Charmley, Seattle, WA (US); Ryan C. Smith, Seattle, WA (US); Rhodora H. Argonza-Barrett, Seattle, WA (US); Matthew P. Fitzgibbon, Bellevue, WA (US); Kai Wang, Bellevue, WA (US)

(73) Assignee: Celltech R&D, Inc. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/512,832

(22) Filed: Jul. 30, 2009

(65) Prior Publication Data

US 2010/0063259 A1    Mar. 11, 2010

Related U.S. Application Data

(60) Continuation of application No. 11/110,977, filed on Apr. 19, 2005, now Pat. No. 7,585,954, which is a division of application No. 10/112,645, filed on Mar. 28, 2002, now abandoned.

(60) Provisional application No. 60/280,514, filed on Mar. 29, 2001.

(51) Int. Cl.
*C07K 16/00* (2006.01)
(52) U.S. Cl. .................................. 530/387.9
(58) Field of Classification Search ........ None
See application file for complete search history.

(56) References Cited

U.S. PATENT DOCUMENTS 7,585,954 B2 * 9/2009 Charmley et al. ........ 530/388.1

FOREIGN PATENT DOCUMENTS

| WO | WO 99/38881 | 8/1999 |
|----|-------------|--------|
| WO | WO 01/29221 | 4/2001 |
| WO | WO 01/53312 | 7/2001 |
| WO | WO 02/46465 | 6/2002 |

OTHER PUBLICATIONS

Abaza et al., Journal of Protein Chemistry 1992, 11(5):433-444.
Attwood Science 200; 290:471-473, 2000.
Colman et al., iResearch in Immunology 1994, 145(1):33-36.
Lederman et al., Molecular immunology 1991, 28:1171-1181.
Menter, A., Cutis, Feb. 1998, 61(25)(2 Suppl.):8-10.
Metzler et al., Nature Structural Biol. 1997; 4:527-531.
Nucleic Acid Sequence Accession No. AK00096, deposited in GenBank on Feb. 22, 2000, NCBI Sequence Viewer [online], http://www.ncbi.nlm.nih.gov [retrieved Apr. 17, 2002], 2 pages.
Nucleic Acid Sequence Accession No. AK10583, deposited in GenBank on Jun. 6, 2000, NCBI Sequence View [online], http://www.ncbi.nlm.nih.gov [retrieved Apr. 17, 2002], 54 pages.
Nucleic Acid Sequence Accession No. AK10583, updated in GenBank on Feb. 22, 2001, NCBI Sequence Viewer [online], http://www.ncbi.nlm.nih.gov [retrieved Apr. 17, 2002], 54 pages.
Skolnick et al. Trends in Biotech. 2000; 18(1):4-39.
Trepicchio, W. et al., J. Clin. Investigation, Dec. 1999, 104(11):1527-1537.
Van Regenmortel, et al. A Companion to Methods of Enzymology 1996, 9:465-472.

* cited by examiner

*Primary Examiner*—Michail A Belyavskyi
(74) *Attorney, Agent, or Firm*—C. Rachal Winger; K&L Gates LLP

(57) ABSTRACT

The present invention provides nucleic acid molecules, polypeptides, antibodies and methods for the diagnosis and/or treatment of psoriasis.

3 Claims, No Drawings

19.5 POLYPEPTIDE ANTIBODIES USEFUL FOR DIAGNOSING OR TREATING PSORIASIS

CROSS-REFERENCE TO RELATED APPLICATION

This application is a continuation of U.S. patent application Ser. No. 11/110,977, filed Apr. 19, 2005, now U.S. Pat. No. 7,585,954, which is a divisional of U.S. patent application Ser. No. 10/112,645, filed Mar. 28, 2002, now abandoned, which claims the benefit of U.S. Provisional Patent Application No. 60/280,514, filed on Mar. 29, 2001, the benefit of which is hereby claimed under 35 U.S.C.§119.

FIELD OF THE INVENTION

The present invention relates generally to polynucleotides, proteins, antibodies and methods for the diagnosis of psoriasis, and/or the amelioration of the symptoms of psoriasis.

BACKGROUND OF THE INVENTION

Psoriasis is a chronic inflammatory dermatosis that affects about 2% of the Caucasian population. It is characterized by hyperproliferation of epidermal cells and inflammation resulting from infiltration of activated T-helper cells and mononuclear cells and release of pro-inflammatory cytokines (Menter and Barker, *Lancet* 338:231, 1991; Barker, *Lancet* 338:227 1991). It may also be associated with arthritis and can present as a severely inflammatory dermatosis in patients with acquired immunodeficiency syndrome (AIDS) (Duvic, *J. Invest. Dermatol.* 95:385 1990). The symptoms of psoriasis include sharply defined erythematosus patches covered with a distinctive scale, hyperproliferation of the epidermis, incomplete differentiation of keratinocytes and dermal inflammation. Clinical variants of psoriasis include erythroderma, seborrheic, inverse, guttate, and photosensitive psoriasis, pustular variants and Reiter's disease.

The role of immunomodulation in psoriasis is supported by the pharmacological action of drugs such as cyclosporine. For example, inhibition of the synthesis of interleukin-2 prevents the proliferation of T-cells and thus their release of cytokines. Mediators of inflammation play a role in the immunoregulation of psoriasis. Currently available methods for treatment include topical therapy, phototherapy, photochemotherapy and systemic therapy and provide, at best, only temporary relief. Topical glucocorticoids are most commonly prescribed as the initial treatment of psoriasis for their anti-inflammatory, antimitotic and antipruritic effects. However, their efficacy is often short term. Crude coal tar is a complex mixture of thousands of hydrocarbon compounds and affects psoriasis by enzyme inhibition and antimitotic action. Although effective, tar stains the skin and has an odor. Anthralin (dithranol) is used topically and inhibits enzyme metabolism and reduces epidermal mitotic turnover. Remission may last for weeks to months. Phototherapy and photochemotherapy entailing the administration of the photosensitizing drug methoxsalen are only temporarily effective, as psoriasis recurs months after this treatment is discontinued. This recurrence indicates that the therapy is palliative rather than curative. Long-term consequences are altered immunologic effects and an increased risk of carcinogenesis.

Methotrexate is the most commonly administered systemic cytotoxic agent for widespread psoriasis. Contraindications are numerous and after withdrawal, psoriatic symptoms may be more severe than during earlier episodes. Hydroxyurea, etretinate, cyclosporine, and AZT are also systemic medications used for the control of psoriasis and all have serious side effects. Clearly, an understanding of the pathogenesis of psoriasis remains an important challenge in dermatologic medical treatment.

Monozygotic twins have significantly higher concordance rates of disease generally than dizygotic twins (Brandrup et al., *Arch. Dermatol.* 114:874 1978; Watson et al., *Arch. Dermatol.* 105:197 1972). Psoriasis has also been reported to aggregate in some families (Pietrzyk et al., *Arch. Dermatol. Res.* 273:295 1982; Karvonen et al., *Ann. Clin. Res.* 8:298 1976; Civatte et al., *Ann. Dermatol. Venereol.* 104:525 1977; Espinoza et al., *J. Rheumatol.* 7:445 1980). The aggregation of psoriasis in families suggests that psoriasis can be inherited as an autosomal dominant trait with penetrance values of 10 to 50%. About 30% of psoriasis patients have a first degree relative with the disease (Barker, 1991).

A need continues to exist in the medical arts for preparations and techniques for both diagnosing and treating psoriasis and psoriasis-like conditions that have less severe side effects and are more effective in treating the source of the disease. The present invention is directed to compositions, including polynucleotides, polypeptides and antibodies and methods for the diagnosis and amelioration of the symptoms of psoriasis.

SUMMARY OF THE INVENTION

In accordance with the foregoing, the present invention provides nucleic acid molecules, polypeptides, antibodies and methods for the diagnosis and/or amelioration of psoriasis.

In one aspect, the present invention provides isolated genomic DNA molecules that encode a polypeptide that is at least 70% identical (such as at least 80% identical, at least 90% identical, or at least 95% identical), to the 19.5 polypeptide that is encoded by SEQ ID NO:1 and that consists of the amino acid sequence set forth in SEQ ID NO:2. In another aspect, the present invention provides isolated genomic DNA molecules that hybridize to the cDNA molecule having the sequence set forth in SEQ ID NO:1 or to the complement of the cDNA molecule of SEQ ID NO:1, under stringent conditions, such as 1×SSC at 55° C. In a related aspect, the present invention provides isolated cDNA molecules that hybridize to the cDNA molecule having the sequence set forth in SEQ ID NO:1 or to the complement of the cDNA molecule of SEQ ID NO:1, under stringent conditions of 0.1×SSC at 60° C.

In another aspect, the present invention provides isolated nucleic acid molecules that comprise a nucleic acid molecule that encodes a 19.5 polypeptide, wherein the encoded 19.5 polypeptide is at least 70% identical (such as at least 80% identical, at least 90% identical, or at least 95% identical) to the 19.5 polypeptide having the sequence set forth in SEQ ID NO:2, and the nucleic acid molecule encoding the 19.5 polypeptide is operably linked to a skin-specific promoter.

In another aspect, the present invention provides vectors (and host cells that contain one or more of the vectors) comprising a nucleic acid molecule that encodes a polypeptide that is at least 70% identical (such as at least 80% identical, at least 90% identical, or at least 95% identical) to the 19.5 polypeptide having the sequence set forth in SEQ ID NO:2. In some embodiments of this aspect of the invention, the nucleic acid molecule that encodes a 19.5 polypeptide is operably linked to a skin-specific promoter.

In another aspect, the present invention provides isolated antibodies (including polyclonal, monoclonal and CDR-grafted antibodies) that bind specifically to a polypeptide consisting of an amino acid sequence that is at least 70% identical (such as at least 80% identical, at least 90% identical, or at least 95% identical) to the amino acid sequence set forth in SEQ ID NO:2.

In yet other aspects, the present invention provides isolated cDNA molecules, such as full-length cDNA molecules (e.g., SEQ ID NO:3), that encode a 19.5-like polypeptide, wherein the 19.5-like polypeptide is at least 70% identical (such as at least 80% identical, at least 90% identical, or at least 95% identical) to the 19.5-like polypeptide having the sequence set forth in SEQ ID NO:4. In another aspect, the present invention provides isolated cDNA molecules that encode a 19.5-like polypeptide and that hybridize to the cDNA molecule having the sequence set forth in SEQ ID NO:3, or to the complement of the cDNA molecule of SEQ ID NO:3, under stringent conditions, such as 1×SSC at 55° C. In a related aspect, the present invention provides isolated cDNA molecules that encode a 19.5-like polypeptide and that hybridize to the cDNA molecule having the sequence set forth in SEQ ID NO:3, or to the complement of the cDNA molecule of SEQ ID NO:3, under stringent conditions of 0.1×SSC at 55° C.

In another aspect, the present invention provides isolated nucleic acid molecules that comprise a nucleic acid molecule that encodes a 19.5-like polypeptide, wherein the encoded 19.5-like polypeptide is at least 70% identical (such as at least 80% identical, at least 90% identical, or at least 95% identical) to the 19.5-like polypeptide having the sequence set forth in SEQ ID NO:4, and the nucleic acid molecule encoding the 19.5-like polypeptide is operably linked to a skin-specific promoter.

In another aspect, the present invention provides vectors (and host cells that contain one or more of the vectors) comprising a cDNA molecule that encodes a polypeptide that is at least 70% identical (such as at least 80% identical, at least 90% identical, or at least 95% identical) to the 19.5-like polypeptide having the sequence set forth in SEQ ID NO:4. In some embodiments of this aspect of the invention, the nucleic acid molecule that encodes a 19.5-like polypeptide is operably linked to a skin-specific promoter.

In another aspect, the present invention provides isolated antibodies (including polyclonal, monoclonal and CDR-grafted antibodies) that bind specifically to a polypeptide consisting of an amino acid sequence that is at least 70% identical (such as at least 80% identical, at least 90% identical, or at least 95% identical) to the 19.5-like polypeptide amino acid sequence set forth in SEQ ID NO:4.

In other aspects the present invention provides methods of diagnosing or predicting the susceptibility to psoriasis in an individual, the methods comprising: (a) obtaining a sample from an individual; (b) determining an expression level of a 19.5 and/or 19.5-like polypeptide in the sample; and (c) diagnosing or predicting the susceptibility of the individual to psoriasis based on the presence or amount of expression of the 19.5 and/or 19.5-like polypeptide(s). In some embodiments, the 19.5 and/or 19.5-like polypeptides are at least 70% identical (such as at least 80% identical, at least 90% identical, or at least 95% identical) to the 19.5 or 19.5-like polypeptides set forth in SEQ ID NO:2 and SEQ ID NO:4, respectively.

In another aspect the present invention provides methods of diagnosing or predicting the susceptibility to psoriasis in an individual, the methods comprising: (a) obtaining a sample from an individual; (b) determining an expression level of a nucleic acid molecule that is at least 70% identical (such as at least 80% identical, at least 90% identical, or at least 95% identical) to a nucleic acid molecule having a sequence set forth in SEQ ID NO:1 or SEQ ID NO:3; and (c) diagnosing or predicting the susceptibility of said individual to psoriasis based on the presence or amount of expression of said nucleic acid molecule.

In another aspect, the present invention provides methods for ameliorating the symptoms and/or progression of psoriasis, the methods comprising administering to an individual suffering from psoriasis an inhibitory amount of a selective inhibitor of at least one polypeptide chosen from the group consisting of 19.5 and 19.5-like, wherein the inhibitory amount causes a reduction in the amount and/or activity of the chosen polypeptide(s). A representative example of a selective inhibitor is an antisense polynucleotide that is complementary to all, or to a portion, of a nucleic acid molecule that encodes a 19.5 or 19.5-like polypeptide.

In another aspect, the present invention provides methods for making an isolated 19.5 or 19.5-like polypeptide of the invention comprising (a) culturing a recombinant host cell, comprising a vector that comprises a nucleic acid molecule encoding a 19.5 and/or 19.5-like polypeptide, under conditions that enable expression of the polypeptide; and (b) recovering the expressed polypeptide.

In yet another aspect, the present invention provides methods for identifying a binding partner of a 19.5 or 19.5-like polypeptide of the invention comprising (a) contacting a 19.5 or 19.5-like polypeptide with a binding partner (such as a monoclonal or polyclonal antibody); and (b) determining whether the binding partner affects a biological activity of the polypeptide.

The methods and compositions of the invention are useful, for example, to identify individuals predisposed to psoriasis, and/or who are suffering from psoriasis, and to ameliorate the symptoms of psoriasis. The methods and compositions of the invention are also useful to identify agents useful for treating psoriasis (such as 19.5 or 19.5-like polypeptide binding partners).

The nucleic acid molecules of the invention are useful, for example, for suppressing the expression of a 19.5 or 19.5-like gene (e.g., by antisense inhibition). Moreover, the nucleic acid molecules of the invention are useful for genetically and/or physically mapping the human genome (such as mapping the location within the human genome of a 19.5 or 19.5-like gene). The proteins of the invention are useful, for example, for enhancing the level of 19.5 or 19.5-like biological activity in a cell or tissue (e.g., by expressing within a cell a nucleic acid molecule of the invention encoding a 19.5 or 19.5-like protein). The antibodies of the invention are useful, for example, for decreasing the level of 19.5 or 19.5-like biological activity in a cell (e.g., by introducing into a cell an antibody that selectively binds to a 19.5 or 19.5-like protein).

All references discussed herein are specifically incorporated in their entirety in all respects.

DETAILED DESCRIPTION OF THE PREFERRED EMBODIMENT

Unless specifically defined herein, all terms used herein have the same meaning as they would to one skilled in the art of the present invention. Practitioners are particularly directed to Sambrook et al. (1989) *Molecular Cloning: A Laboratory Manual,* 2nd ed., Cold Spring Harbor Press, Plainsview, N.Y. (1989), and Ausubel et al., *Current Protocols in Molecular Biology* (Supplement 47), John Wiley & Sons, New York (1999), for definitions and terms of the art.

The letter "n" within any nucleic acid sequence set forth herein means that the identity of the nucleic acid residue represented by "n" was not determined.

As used herein, the term "isolated" used with respect to a nucleic acid molecule or polypeptide of the invention means a molecule that is substantially free from cellular components that are associated with the nucleic acid molecule or polypeptide as it is found in nature. As used in this context, the term "substantially free from cellular components" means that the nucleic acid molecule or polypeptide is purified to a purity level of greater than 80% (such as greater than 90%, greater than 95%, or greater than 99%). Moreover, the terms "isolated nucleic acid molecule" and "isolated polypeptide" include nucleic acid molecules and polypeptides which do not naturally occur, and have been produced by synthetic means. An isolated nucleic acid molecule or polypeptide generally resolves as a single, predominant, band by gel electrophoresis, and yields a nucleotide or amino acid sequence profile consistent with the presence of a predominant nucleic acid molecule or polypeptide.

As used herein, the term "19.5 polypeptide" refers to a protein that is (a) at least 70% identical to the 19.5 polypeptide of SEQ ID NO:2, (b) has the same biological function as the 19.5 polypeptide having the amino acid sequence set forth in SEQ ID NO:2 and (c) is expressed predominantly or exclusively in human skin.

As used herein, the term "19.5-like polypeptide" refers to a protein that is (a) at least 70% identical to the 19.5-like polypeptide of SEQ ID NO:4, (b) has the same biological function as the 19.5-like polypeptide having the amino acid sequence set forth in SEQ ID NO:4 and (c) is expressed predominantly or exclusively in human skin.

The term "percent identity" or "percent identical" when used in connection with the nucleic acid molecules and polypeptides of the present invention, is defined as the percentage of nucleic acid residues in a candidate nucleic acid sequence, or the percentage of amino acid residues in a candidate polypeptide sequence, that are identical with a subject nucleic acid sequence or polypeptide sequence (such as the nucleic acid sequence set forth in SEQ ID NO:1, or the amino acid sequence set forth in SEQ ID NO:2), after aligning the candidate and subject sequences to achieve the maximum percent identity, and not considering any nucleic acid residue substitutions as part of the nucleic acid sequence identity. When making the comparison, no gaps are introduced into the candidate polynucleotide sequence or polypeptide sequence in order to achieve the best alignment.

For example, if a 100 base pair subject nucleic acid sequence is aligned with a 100 base pair candidate portion of a larger DNA molecule (such as a genomic clone), and 80% of the nucleic acid residues in the 100 base pair candidate portion align with the identical nucleic acid residues in the 100 base pair subject nucleic acid sequence, then the 100 base pair candidate portion of the larger DNA molecule is 80% identical to the subject nucleic acid sequence.

Nucleic acid sequence identity can be determined in the following manner. The subject nucleic acid sequence is used to search a nucleic acid sequence database, such as the GenBank database (accessible at web site http://www.ncbi.nlm.nih.gov/blast/), using the program BLASTM version 2.1 (based on Altschul et al., *Nucleic Acids Research* 25:3389-3402 (1997)). The program is used in the ungapped mode. Default filtering is used to remove sequence homologies due to regions of low complexity. The default parameters of BLASTM are utilized.

Amino acid sequence identity can be determined in the following manner. The subject polypeptide sequence is used to search a polypeptide sequence database, such as the GenBank database (accessible at web site http://www.ncbi.nlm.nih.gov/blast/), using the BLASTP program. The program is used in the ungapped mode. Default filtering is used to remove sequence homologies due to regions of low complexity. The default parameters of BLASTP are utilized. Filtering for sequences of low complexity utilize the SEG program.

The term "hybridize under stringent conditions", and grammatical equivalents thereof, refers to the ability of a nucleic acid molecule to hybridize to a target nucleic acid molecule (such as a target nucleic acid molecule immobilized on a DNA or RNA blot, such as a Southern blot or Northern blot) under defined conditions of temperature and salt concentration. With respect to nucleic acid molecules greater than about 100 bases in length, typical stringent hybridization conditions are no more than 25° C. to 30° C. (for example, 10° C.) below the melting temperature (Tm) of the native duplex (see generally, Sambrook et al., *Molecular Cloning: A Laboratory Manual*, 2nd Ed. Cold Spring Harbor Press, 1987; Ausubel et al., *Current Protocols in Molecular Biology*, Greene Publishing, 1987). Tm for nucleic acid molecules greater than about 100 bases can be calculated by the formula $Tm=81.5+0.41\% (G+C-\log (Na^+)$.

With respect to nucleic acid molecules having a length less than 100 bases, exemplary stringent hybridization conditions are 5° to 10° C. below Tm. On average, the Tm of a nucleic acid molecule of length less than 100 by is reduced by approximately (500/oligonucleotide length) degrees centigrade.

As used herein, the term "oligonucleotide" refers to a nucleic acid molecule of up to 100 bases.

The term "complement" when used in connection with a nucleic acid molecule refers to the complementary nucleic acid sequence as determined by Watson-Crick base pairing. For example, the complement of the nucleic acid sequence 5'CCATG3' is 5'CATGG3'.

The term "vector" refers to a nucleic acid molecule, usually double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing and translating the insert nucleic acid molecule into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. Many molecules of the polypeptide (if any) encoded by the insert nucleic acid molecule can thus be rapidly synthesized.

The term "antibody" encompasses polyclonal and monoclonal antibody preparations, CDR-grafted antibody preparations, as well as preparations including hybrid antibodies, altered antibodies, F(AB)'$_2$ fragments, F(AB) molecules, Fv fragments, single domain antibodies, chimeric antibodies and functional fragments thereof which exhibit immunological binding properties of the parent antibody molecule. The antibodies can also be humanized.

The term "sample" when used in connection with the methods of the invention for diagnosing or predicting the susceptibility to psoriasis in an individual, means any biological fluid, cell, tissue, organ or portion thereof, that includes or potentially includes a 19.5 or 19.5-like nucleic acid or polypeptide. The term includes samples present in an individual as well as samples obtained or derived from an individual. For example, a sample can be a histologic section of a specimen obtained by biopsy, or cells that are placed in or adapted to tissue culture. A sample can be a subcellular fraction or extract, or a purified or crude nucleic acid or protein preparation.

The term "binding partner" when used in reference to a 19.5 or 19.5-like polypeptide, means a composition such as a macromolecule, that selectively binds a 19.5 or 19.5-like polypeptide, or fragment thereof. For example, a binding partner can be a monoclonal or polyclonal antibody that selectively binds with high affinity to a 19.5 or 19.5-like polypeptide, without substantial cross-reactivity with other polypeptides that are unrelated to 19.5 or 19.5-like polypeptides. The affinity of a binding partner that selectively binds to a 19.5 or 19.5-like polypeptide is generally greater than about $10^{-5}$M, and more usually greater than about $10^{-6}$M. High affinity interactions are preferred, and are generally greater than about $10^{-8}$M to $10^{-9}$M. Representative examples of binding partners include polyclonal or monoclonal antibodies, CDR-grafted antibodies, peptides, polynucleotides, nucleic acids, nucleic acid derivatives, steroids or steroid analogues, small organic molecules, identified, for example, by affinity screening of a small molecule library.

In one aspect, the present invention relates to isolated nucleic acid molecules, such as isolated genomic DNA molecules that encode a 19.5 polypeptide, and isolated cDNA molecules that encode a 19.5-like polypeptide. The nucleic acid molecules of this aspect of the invention can be isolated by using a variety of cloning techniques known to those of ordinary skill in the art. Thus, for example, all, or portions of, the nucleic acid molecules having the sequences set forth in SEQ ID NO:1 (encoding a 19.5 polypeptide) or SEQ ID NO:3 (encoding a 19.5-like polypeptide) can be used as a hybridization probe to screen a genomic or cDNA library, such as a human skin cDNA library. The technique of hybridizing radiolabelled nucleic acid probes to nucleic acids immobilized on nitrocellulose filters or nylon membranes can be used to screen the genomic or cDNA library. Exemplary hybridization and wash conditions are: hybridization at 65° C. in 5.0×SSC, 0.5% sodium dodecyl sulfate Denhardt's solution; washing (three washes of twenty minutes each at 55° C.) in 1.0×SSC, 1% (w/v) sodium dodecyl sulfate, and optionally one wash in 0.1×SSC, 1% (w/v) sodium dodecyl sulfate, at 60° C.

Again, by way of example, nucleic acid molecules of this aspect of the invention can be isolated by the polymerase chain reaction (PCR) described in *The Polymerase Chain Reaction* (K. B. Mullis et al., eds. 1994), incorporated herein by reference. Gobinda et al (*PCR Methods Applic.* 2:318-22 [1993]), incorporated herein by reference, disclose "restriction-site PCR" as a direct method which uses universal primers to retrieve unknown sequence adjacent to a known locus. First, genomic DNA is amplified in the presence of a linker-primer, that is homologous to a linker sequence ligated to the ends of the genomic DNA fragments, and in the presence of a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Further, by way of example, inverse PCR permits acquisition of unknown sequences starting with primers based on a known region (Triglia T. et al., *Nucleic Acids Res.* 16:8186 [1988], incorporated herein by reference). The method uses several restriction enzymes to generate a suitable fragment in the known region of a gene. The fragment is then circularized by intramolecular ligation and used as a PCR template. Divergent primers are designed from the known region.

By way of non-limiting example, representative PCR reaction conditions for amplifying nucleic acid molecules encoding a 19.5 polypeptide from genomic DNA are as follows. The following reagents are mixed in a tube (on ice) to form the PCR reaction mixture: DNA template (e.g., up to 1 µg genomic DNA, or up to 0.1 µg cDNA), 0.1-0.3 mM dNTPs, 5 µl 10×PCR buffer (10×PCR buffer contains 500 mM KCl, 15 mM $MgCl_2$, 100 mM Tris-HCl, pH 8.3), 50 pmol of each PCR primer (PCR primers are typically greater than 20 by in length), 2.5 units of Taq DNA polymerase (Perkin Elmer, Norwalk, Conn.) and deionized water to a final volume of 50 µl. The tube containing the reaction mixture is placed in a thermocycler and a thermocycler program is run as follows. Denaturation at 94° C. for 2 minutes, then 30 cycles of: 94° C. for 30 seconds, 50° C. to 65° C. for 30 seconds, and 72° C. for 30 seconds to two and one-half minutes.

By way of example, the nucleic acid molecules of the invention are useful as hybridization probes in diagnostic procedures. The particular application and degree of desired specificity will be one consideration well known to those skilled in the art in selecting a probe. Untranslated region sequences are useful regions to construct probes since there is little evolutionary pressure to conserve non-coding domains.

Hybridization probes can be produced recombinantly or chemically synthesized using methods well known in the art. Additionally, hybridization probes can be labeled with a variety of detectable labels including, for example, radioisotopes, fluorescent tags, reporter enzymes, biotin and other ligands. Such detectable labels can additionally be coupled with, for example, colorimetric or photometric indicator substrate for spectrophotometric detection. Methods for labeling and detecting such probes are well known in the art and can be found described in, for example, Sambrook et al., supra, and Ausubel et al., supra.

In another aspect, the present invention is directed to regulatory nucleic acid sequences that are operably linked to a 19.5 polypeptide gene, or to a 19.5-like polypeptide gene. The term "regulatory nucleic acid sequence" refers to nucleic acid sequences located upstream (5' non-coding sequences), within, or downstream (3' non-coding sequences) of a coding sequence, and which influence the transcription, RNA processing or stability, or translation of the associated coding sequence. Regulatory sequences include, but are not limited to, enhancers, promoters, translation leader sequences, introns, and polyadenylation signal sequences.

"Promoter" refers to a DNA sequence involved in controlling the expression of a coding sequence or functional RNA. In general, a coding sequence is located 3' to a promoter sequence. The term "promoter" includes a minimal promoter that is a short DNA sequence comprised of a TATA-box and other sequences that serve to specify the site of transcription initiation, to which other regulatory elements may be added for control of expression. "Promoter" also refers to a nucleic acid sequence that includes a minimal promoter plus other regulatory elements that are capable of controlling the expression of a coding sequence or functional RNA. This type of promoter sequence typically consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

One aspect of the present invention provides isolated nucleic acid molecules that comprise a nucleic acid molecule that encodes a 19.5 polypeptide or a 19.5-like polypeptide, wherein the encoded 19.5 polypeptide, or 19.5-like polypeptide, is at least 70% identical (such as at least 80% identical, at least 90% identical, or at least 95% identical) to the 19.5 polypeptide having the sequence set forth in SEQ ID NO:2, or to the 19.5-like polypeptide having the sequence set forth in SEQ ID NO:4, respectively. Further, the nucleic acid molecule encoding the 19.5 polypeptide, or 19.5-like polypeptide, is operably linked to a skin-specific promoter. Any promoter that is specifically or predominantly expressed in one or more skin cell types is useful in this aspect of the invention.

In another aspect, the invention provides vectors comprising: (a) a nucleic acid molecule that encodes a polypeptide that is at least 70% identical (such as at least 80% identical, at least 90% identical, or at least 95% identical) to the 19.5 polypeptide having the sequence set forth in SEQ ID NO:2; and/or (b) a cDNA molecule that encodes a polypeptide that is at least 70% identical (such as at least 80% identical, at least 90% identical, or at least 95% identical) to the 19.5-like polypeptide having the sequence set forth in SEQ ID NO:4.

The construction of suitable vectors containing DNA encoding, for example, replication sequences, regulatory sequences, phenotypic selection genes and a nucleic acid molecule encoding a 19.5 polypeptide, or a 19.5-like polypeptide, can be prepared using standard recombinant DNA procedures. Isolated plasmids and DNA fragments are cleaved, tailored, and ligated together in a specific order to generate the desired vectors, as is well known in the art (see, for example, Sambrook et al., supra).

The choice of vector is dependent, for example, upon the method that would be used to transform the host cells and the desired selection markers. The skilled artisan is well aware of the genetic elements that can be included on the vector in order to successfully transform, select and propagate host cells containing the vector. For example, a vector may also include any other necessary regulatory sequences such as terminators (Guerineau et al., *Mol. Gen. Genet.* 226:141-144 [1991]; Proudfoot, *Cell* 64:671-674 [1991]; Sanfacon et al., *Genes & Dev.* 5:141-149 [1991]; Mogen et al., *Plant Cell* 2:1261-1272 [1990]; Munroe et al., *Gene* 91:151-158 [1990]; Ballas et al., *Nucleic Acids Res.* 17:7891-7903 [1989]; Joshi et al., *Nucleic Acid Res.* 15:9627-9639 [1987]); nuclear localization signals (Kalderon et al., *Cell* 39:499-509 [1984]; Lassner et al., *Plant Mol. Biol.* 17:229-234 [1991]); introns (Luehrsen & Walbot, *Mol. Gen. Genet.*, 225:81-93 [1991]) and the like, operably linked to the nucleotide sequence encoding the transactivator and/or the toxic product. It may also be beneficial to include 5' leader sequences. Such leader sequences can act to enhance translation. Translational leaders are known in the art and include Picornavirus leaders, for example, Encephalomyocarditis leader (Elroy-Stein et al., *Proc. Natl. Acad. Sci. USA* 86:6126-6130 [1989]).

The invention also provide host cells that contain one or more vectors of the invention. A vector of the invention can be introduced into any suitable host cell, such as animal (including human) cells, insect cells, plant cells and bacterial cells. Any art-recognized gene delivery method can be used to introduce a vector of the invention into one or more cells for expression therein, including: transduction, transfection, transformation, direct injection, electroporation, virus-mediated gene delivery, amino acid-mediated gene delivery, biolistic gene delivery, lipofection and heat shock. See, generally, Sambrook et al., supra. Non-viral methods of gene delivery into cells are disclosed in Huang, L., Hung, M-C, and Wagner, E., *Non-Viral Vectors for Gene Therapy*, Academic Press, San Diego, Calif. (1999), which is incorporated herein by reference.

For example, vectors can be introduced into cells in situ, or after removal of the cells from the body, by means of viral vectors. For example, retroviruses are RNA viruses that have the ability to insert their genes into host cell chromosomes after infection. Retroviral vectors have been developed that lack the genes encoding viral proteins, but retain the ability to infect cells and insert their genes into the chromosomes of the target cell (A. D. Miller, *Hum. Gen. Ther.* 1:5-14 (1990)). Adenoviral vectors are designed to be administered directly to patients. Unlike retroviral vectors, adenoviral vectors do not integrate into the chromosome of the host cell. Instead, genes introduced into cells using adenoviral vectors are maintained in the nucleus as an extrachromosomal element (episome) that persists for a limited time period. Adenoviral vectors will infect dividing and non-dividing cells in many different tissues in vivo including airway epithelial cells, endothelial cells, hepatocytes and various tumors (B. C. Trapnell, *Adv Drug Del Rev.* 12:185-199 (1993)).

Another viral vector is the herpes simplex virus; a large, double-stranded DNA virus that has been used in some initial applications to deliver therapeutic genes to neurons and could potentially be used to deliver therapeutic genes to some forms of brain cancer (D. S. Latchman, *Mol. Biotechnol.* 2:179-95 (1994)). Recombinant forms of the vaccinia virus can accommodate large inserts and are generated by homologous recombination. To date, this vector has been used to deliver interleukins (ILs), such as human IL-1β and the costimulatory molecules B7-1 and B7-2 (G. R. Peplinski et al., *Ann. Surg. Oncol.* 2:151-9 (1995); Hodge, J. W. et al., *Cancer Res.* 54:5552-55 (1994)).

Vectors can be directly introduced into subjects in need thereof. (See, e.g., F. D. Ledley, *Hum. Gene Ther.* 6:1129-1144 (1995)). The vector DNA is taken up by cells within the body and can direct expression of recombinant proteins. Typically vector DNA is delivered to cells in the form of liposomes in which the DNA is associated with one or more lipids, such as DOTMA (1,2,-diolcyloxypropyl-3-trimethyl ammonium bromide) and DOPE (dioleoylphosphatidylethanolamine). Formulations with DOTMA have been shown to provide expression in pulmonary epithelial cells in animal models (K. L. Brigham et al., *Am. J. Med. Sci,* 298:278-281 (1989); A. B. Canonico et al., *Am. J. Respir. Cell. Mol. Biol.* 10:24-29 (1994)). Additionally, studies have demonstrated that intramuscular injection of plasmid DNA formulated with 5% PVP (50,000 kDa) increases the level of reporter gene expression in muscle as much as 200-fold over the levels found with injection of DNA in saline alone (R. J. Mumper et al., *Pharm. Res.* 13:701-709 (1996); R. J. Mumper et al., *Proc. Intern. Symp. Cont. Rol. Bioac. Mater.* 22:325-326 (1995)). Intramuscular administration of plasmid DNA results in gene expression that lasts for many months (J. A. Wolff et al., *Hum. Mol. Genet.* 1:363-369 (1992); M. Manthorpe et al., *Hum. Gene Ther.* 4:419-431 (1993); G. Ascadi et al., *New Biol.* 3:71-81 (1991), D. Gal et al., *Lab. Invest.* 68:18-25 (1993)).

Additionally, uptake and expression of DNA has also been observed after direct injection of plasmid into the thyroid (M. Sikes et al., *Hum. Gene Ther.* 5:837-844 (1994)) and synovium (J. Yovandich et al., *Hum. Gene Ther.* 6:603-610 (1995)). Lower levels of gene expression have been observed after interstitial injection into liver (M. A. Hickman et al., *Hum. Gene Ther.* 5:1477-1483 (1994)), skin (E. Raz et al., *Proc. Natl. Acad. Sci.* 91:9519-9523 (1994)), instillation into the airways (K. B. Meyer et al., *Gene Therapy* 2:450-460 (1995)), application to the endothelium (G. D. Chapman et al., *Circulation Res.* 71:27-33 (1992); R. Riessen et al., *Human Gene Therapy,* 4:749-758 (1993)), and after intravenous administration (R. M. Conry et al., *Cancer Res.* 54:1164-1168 (1994)).

Various devices have been developed for enhancing the availability of DNA to the target cell. A simple approach is to contact the target cell physically with catheters or implantable materials containing DNA (G. D. Chapman et al., *Circulation Res.* 71:27-33 (1992)). Another approach is to utilize needle-free, jet injection devices which project a column of liquid directly into the target tissue under high pressure. (P. A. Furth et al., *Anal Biochem.* 20:365-368 (1992); (H. L. Vahlsing et al., *J. Immunol. Meth.* 175:11-22 (1994); (F. D. Ledley et al., *Cell Biochem.* 18A:226 (1994)).

Another device for gene delivery is the "gene gun" or Biolistic™, a ballistic device that projects DNA-coated micro-particles directly into the nucleus of cells in vivo. Once within the nucleus, the DNA dissolves from the gold or tungsten microparticle and can be expressed by the target cell. This method has been used effectively to transfer genes directly into the skin, liver and muscle (N. S. Yang et al., *Proc. Natl. Acad. Sci.* 87:9568-9572 (1990); L. Cheng et al., *Proc. Natl. Acad. Sci. USA.* 90:4455-4459 (1993); R. S. Williams et al., *Proc. Natl. Acad. Sci.* 88:2726-2730 (1991)).

Another approach to targeted gene/vector delivery is the use of molecular conjugates, which consist of protein or synthetic ligands to which a nucleic acid- or DNA-binding agent has been attached for the specific targeting of nucleic acids to cells (R. J. Cristiano et al., *Proc. Natl. Acad. Sci. USA* 90:11548-52 (1993); B. A. Bunnell et al., *Somat. Call Mol. Genet.* 18:559-69 (1992); M. Cotton et al., *Proc. Natl. Acad. Sci. USA* 89:6094-98 (1992)). Once the DNA is coupled to the molecular conjugate, a protein-DNA complex results. This gene delivery system has been shown to be capable of targeted delivery to many cell types through the use of different ligands (R. J. Cristiano et al., *Proc. Natl. Acad. Sci. USA* 90:11548-52 (1993)). For example, the vitamin folate has been used as a ligand to promote delivery of plasmid DNA into cells that overexpress the folate receptor (e.g., ovarian carcinoma cells) (S. Gottschalk et al., *Gene Ther.* 1:185-91 (1994)). The malaria circumsporozoite protein has been used for the liver-specific delivery of genes under conditions in which ASOR receptor expression on hepatocytes is low, such as in cirrhosis, diabetes, and hepatocellular carcinoma (Z. Ding et al., *J. Biol. Chem.* 270:3667-76 (1995)). The overexpression of receptors for epidermal growth factor (EGF) on cancer cells has allowed for specific uptake of EGF/DNA complexes by lung cancer cells (R. Cristiano et al., *Cancer Gene Ther.* 3:4-10 (1996)).

Prokaryotic host cells or other host cells with rigid cell walls can be transformed, for example, using the calcium chloride method as described in section 1.82 of Sambrook et al., supra. Additionally, electroporation may be used for transformation of these cells. Prokaryote transformation techniques are set forth in Dower, W. J., in *Genetic Engineering, Principles and Methods,* 12:275-296, Plenum Publishing Corp. (1990); Hanahan et al., *Meth. Enzymol.,* 204:63 (1991).

In another aspect, the present invention is directed to antibodies that bind specifically to one or more 19.5 or 19.5-like polypeptides, and/or to fragments thereof. By way of representative example, antigen useful for raising antibodies can be prepared in the following manner. A nucleic acid molecule (such as a cDNA molecule) encoding a 19.5 or 19.5-like polypeptide is cloned into a plasmid vector, such as a Bluescript plasmid (available from Stratagene, Inc., La Jolla, Calif.). The recombinant vector is then introduced into an *E. coli* strain (such as *E. coli* XL1-Blue, also available from Stratagene, Inc.) and the polypeptide encoded by the nucleic acid molecule is expressed in *E. coli* and then purified. For example, *E. coli* XL1-Blue harboring a Bluescript vector including a cDNA molecule of interest is grown overnight at 37° C. in LB medium containing 100 µg ampicillin/ml. A 50 µl aliquot of the overnight culture is used to inoculate 5 ml of fresh LB medium containing ampicillin, and the culture grown at 37° C. with vigorous agitation to $A_{600}$=0.5 before induction with 1 mM IPTG. After an additional two hours of growth, the suspension is centrifuged (1000×g, 15 min, 4° C.), the media removed, and the pelleted cells resuspended in 1 ml of cold buffer that preferably contains 1 mM EDTA and one or more proteinase inhibitors. The cells can be disrupted by sonication with a microprobe. The chilled sonicate is cleared by centrifugation and the expressed, recombinant polypeptide purified from the supernatant by art-recognized protein purification techniques, such as those described herein.

Alternatively, polypeptides can be prepared using peptide synthesis methods that are well known in the art. The synthetic polypeptides can then be used to prepare antibodies. Direct peptide synthesis using solid-phase techniques (Stewart et al., Solid-Phase Peptide Synthesis, W H Freeman Co, San Francisco Calif. (1969); Merrifield, *J. Am. Chem. Soc.* 85:2149-2154 (1963) is an alternative to recombinant or chimeric peptide production. Automated synthesis may be achieved, for example, using Applied Biosystems 431A Peptide Synthesizer (Foster City, Calif.) in accordance with the instructions provided by the manufacturer. Additionally the 19.5 and 19.5-like polypeptide sequences, or any fragment thereof, may be mutated during direct synthesis and, if desired, combined using chemical methods with other amino acid sequences. The polypeptides used to induce specific antibodies may have an amino acid sequence consisting of at least five amino acids and preferably at least 10 amino acids. Short stretches of amino acid sequence may be attached with those of another polypeptide, and the chimeric polypeptide used for antibody production. Alternatively, the polypeptide may be of sufficient length to contain an entire domain for antibody recognition.

Representative examples of art-recognized techniques for purifying, or partially purifying, polypeptides from biological material (such as from prokaryotic cells that express the desired polypeptide(s) are: exclusion chromatography, ion-exchange chromatography, hydrophobic interaction chromatography, reversed-phase chromatography and immobilized metal affinity chromatography.

Hydrophobic interaction chromatography and reversed-phase chromatography are two separation methods based on the interactions between the hydrophobic moieties of a sample and an insoluble, immobilized hydrophobic group present on the chromatography matrix. In hydrophobic interaction chromatography the matrix is hydrophilic and is substituted with short-chain phenyl or octyl nonpolar groups. The mobile phase is usually an aqueous salt solution. In reversed phase chromatography the matrix is silica that has been substituted with longer n-alkyl chains, usually $C_8$ (octylsilyl) or $C_{18}$ (octadecylsilyl). The matrix is less polar than the mobile phase. The mobile phase is usually a mixture of water and a less polar organic modifier.

Separations on hydrophobic interaction chromatography matrices are usually done in aqueous salt solutions, which generally are nondenaturing conditions. Samples are loaded onto the matrix in a high-salt buffer and elution is by a descending salt gradient. Separations on reversed-phase media are usually done in mixtures of aqueous and organic solvents, which are often denaturing conditions. In the case of polypeptide and/or peptide purification, hydrophobic interaction chromatography depends on surface hydrophobic groups and is carried out under conditions which maintain the integrity of the polypeptide molecule. Reversed-phase chromatography depends on the native hydrophobicity of the polypeptide and is carried out under conditions which expose nearly all hydrophobic groups to the matrix, i.e., denaturing conditions.

Ion-exchange chromatography is designed specifically for the separation of ionic or ionizable compounds. The stationary phase (column matrix material) carries ionizable functional groups, fixed by chemical bonding to the stationary phase. These fixed charges carry a counterion of opposite sign. This counterion is not fixed and can be displaced. Ion-exchange chromatography is named on the basis of the sign of the displaceable charges. Thus, in anion ion-exchange chromatography the fixed charges are positive and in cation ion-exchange chromatography the fixed charges are negative.

Retention of a molecule on an ion-exchange chromatography column involves an electrostatic interaction between the fixed charges and those of the molecule, binding involves replacement of the nonfixed ions by the molecule. Elution, in turn, involves displacement of the molecule from the fixed charges by a new counterion with a greater affinity for the fixed charges than the molecule, and which then becomes the new, nonfixed ion.

The ability of counterions (salts) to displace molecules bound to fixed charges is a function of the difference in affinities between the fixed charges and the nonfixed charges of both the molecule and the salt. Affinities in turn are affected by several variables, including the magnitude of the net charge of the molecule and the concentration and type of salt used for displacement.

Solid-phase packings used in ion-exchange chromatography include cellulose, dextrans, agarose, and polystyrene. The exchange groups used include DEAE (diethylaminoethyl), a weak base, that will have a net positive charge when ionized and will therefore bind and exchange anions; and CM (carboxymethyl), a weak acid, with a negative charge when ionized that will bind and exchange cations. Another form of weak anion exchanger contains the PEI (polyethyleneimine) functional group. This material, most usually found on thin layer sheets, is useful for binding polypeptides at pH values above their pI. The polystyrene matrix can be obtained with quaternary ammonium functional groups for strong base anion exchange or with sulfonic acid functional groups for strong acid cation exchange. Intermediate and weak ion-exchange materials are also available. Ion-exchange chromatography need not be performed using a column, and can be performed as batch ion-exchange chromatography with the slurry of the stationary phase in a vessel such as a beaker.

Gel filtration is performed using porous beads as the chromatographic support. A column constructed from such beads will have two measurable liquid volumes, the external volume, consisting of the liquid between the beads, and the internal volume, consisting of the liquid within the pores of the beads. Large molecules will equilibrate only with the external volume while small molecules will equilibrate with both the external and internal volumes. A mixture of molecules (such as proteins) is applied in a discrete volume or zone at the top of a gel filtration column and allowed to percolate through the column. The large molecules are excluded from the internal volume and therefore emerge first from the column while the smaller molecules, which can access the internal volume, emerge later. The volume of a conventional matrix used for protein purification is typically 30 to 100 times the volume of the sample to be fractionated. The absorbance of the column effluent can be continuously monitored at a desired wavelength using a flow monitor.

A technique that is often applied to the purification of polypeptides is High Performance Liquid Chromatography (HPLC). HPLC is an advancement in both the operational theory and fabrication of traditional chromatographic systems. HPLC systems for the separation of biological macromolecules vary from the traditional column chromatographic systems in three ways; (1) the column packing materials are of much greater mechanical strength, (2) the particle size of the column packing materials has been decreased 5- to 10-fold to enhance adsorption-desorption kinetics and diminish bandspreading, and (3) the columns are operated at 10-60 times higher mobile-phase velocity. Thus, by way of non-limiting example, HPLC can utilize exclusion chromatography, ion-exchange chromatography, hydrophobic interaction chromatography, reversed-phase chromatography and immobilized metal affinity chromatography. Art-recognized techniques for the purification of proteins and peptides are set forth in Methods in Enzymology, Vol. 182, Guide to Protein Purification, Murray P. Deutscher, ed (1990).

Methods for preparing monoclonal and polyclonal antibodies are well known to those of ordinary skill in the art and are set forth, for example, in chapters five and six of *Antibodies A Laboratory Manual*, E. Harlow and D. Lane, Cold Spring Harbor Laboratory (1988). In one representative example, polyclonal antibodies specific for a purified polypeptide are raised in a New Zealand rabbit implanted with a whiffle ball. One µg of polypeptide is injected at intervals directly into the whiffle ball granuloma. A representative injection regime is injections (each of 1 µg protein) at day 1, day 14 and day 35. Granuloma fluid is withdrawn one week prior to the first injection (preimmune serum), and forty days after the final injection (postimmune serum).

Antibody production includes not only the stimulation of an immune response by injection into animals, but also analogous processes such as the production of synthetic antibodies, the screening of recombinant immunoglobulin libraries for specific-binding molecules (Orlandi et al., *Proc. Natl. Acad. Sci. USA* 86:3833, 1989, or Huse et al. *Science* 256:1275, 1989), or the in vitro stimulation of lymphocyte populations.

Current technology (Winter and Milstein, *Nature* 349:293, 1991) provides for a number of highly specific binding reagents based on the principles of antibody formation. These techniques may be adapted to produce molecules which specifically bind to 19.5 or 19.5-like polypeptides or fragments thereof. Antibodies or other appropriate molecules generated against a specific immunogenic peptide fragment or polypeptide can be used in Western analysis, enzyme-linked immunosorbent assays (ELISA) or similar tests to establish the presence of, or to quantitate amounts of, 19.5 or 19.5-like polypeptide in normal, diseased, or therapeutically treated cells or tissues. Variations on any procedure known in the art for the measurement of polypeptides can be used in the practice of the instant invention. Such procedures include but are not limited to competitive and non-competitive assay systems using techniques such as radioimmunoassays, ELISA (enzyme linked immunoabsorbent assay), sandwich immunoassays, agglutination assays, complement fixation assays, immunoradiometric assays, fluorescent immunoassays, protein A immunoassays, immunoelectrophoresis assays and the like.

In other aspects the present invention provides methods of diagnosing or predicting the susceptibility to psoriasis in an individual. In one aspect, the methods of diagnosing or predicting the susceptibility to psoriasis in an individual comprise: (a) obtaining a sample from an individual; (b) determining an expression level of a 19.5 and/or 19.5-like polypeptide in the sample; and (c) diagnosing or predicting the susceptibility of the individual to psoriasis based on the presence or amount of expression of the 19.5 and/or 19.5-like polypeptide(s). In some embodiments, the 19.5 and/or 19.5-like polypeptides are at least 70% identical (such as at least 80% identical, at least 90% identical, or at least 95% identical) to the 19.5 or 19.5-like polypeptides set forth in SEQ ID NO:2 and SEQ ID NO:4, respectively.

In another aspect the methods of diagnosing or predicting the susceptibility to psoriasis in an individual, the methods comprise: (a) obtaining a sample from an individual; (b) determining an expression level of a nucleic acid molecule that is at least 70% identical (such as at least 80% identical, at least 90% identical, or at least 95% identical) to a nucleic acid molecule having a sequence set forth in SEQ ID NO:1 or SEQ ID NO:3; and (c) diagnosing or predicting the susceptibility of said individual to psoriasis based on the presence or amount of expression of said nucleic acid molecule.

The diagnostic methods of the invention are applicable for use with a variety of different types of samples isolated or obtained from an individual. For example, samples applicable for use in one or more diagnostic formats of the invention, include tissue and cell samples. A tissue or cell sample can be obtained, for example, by biopsy or surgery. As described below, and depending on the format of the method, the tissue can be used whole or subjected to various methods known in the art to disassociate the sample into smaller pieces, cell aggregates or individual cells. Additionally, when combined with amplification methods such as polymerase chain reaction (PCR), a single skin cell sample is sufficient for use in diagnostic assays of the invention which employ nucleic acid hybridization detection methods. Similarly, when measuring polypeptide levels or activity levels, amplification of the signal with enzymatic coupling or photometric enhancement can be employed using only a few or a small number of cells.

Whole tissue obtained from a skin biopsy or surgery is one example of a skin cell sample. Whole tissue skin samples can be assayed employing any of the formats described below. For example, the skin tissue sample can be mounted and hybridized in situ with a nucleic acid probe of the present invention. Similar histological formats employing protein detection methods and in situ activity assays also can be used to detect 19.5 and/or 19.5-like polypeptides in whole skin tissue cell samples. Polypeptide detection methods include, for example, staining with antibodies specific for a target polypeptide (e.g., 19.5 or 19.5-like) and activity assays which result in the deposition of a polypeptide end product at the site of enzyme activity in the sample. Such histological methods as well as others are well known to those skilled in the art and are applicable for use in the diagnostic methods of the invention using whole tissue as the source of the sample. Methods for preparing and mounting the samples are similarly well known in the art.

Individual keratinocyte cells and cell aggregates from an individual having, or suspected of having, psoriasis is another example of a skin cell sample which can be analyzed for increased or decreased expression of 19.5 and/or 19.5-like polypeptides or activity. The cells can be grown in culture and analyzed in situ using procedures such as those described above. The expression level can be determined by, for example, binding agents specific for 19.5 and/or 19.5-like polypeptides, or by hybridization to a probe specific to at least 15 contiguous nucleotides of a nucleic acid molecule encoding a 19.5 and/or 19.5-like polypeptide. Other methods for measuring the expression level of 19.5 and/or 19.5-like polypeptides, or nucleic acid molecules encoding 19.5 and/or 19.5-like polypeptides, in whole cell samples are known in the art and are similarly applicable in any of the diagnostic formats described below.

The sample obtained from an individual also can be analyzed for increased or decreased expression of 19.5 and/or 19.5-like polypeptides by lysing the cell and measuring the expression levels of 19.5 and/or 19.5-like polypeptides, or nucleic acid molecules encoding 19.5 and/or 19.5-like polypeptides, in the lysate, a fractionated portion thereof, or a purified component thereof, such as by using any of the diagnostic formats described below. For example, if a hybridization format is used, RNA that encodes a 19.5 and/or 19.5-like polypeptide can be amplified directly from the lysate using PCR, or other amplification procedures well known in the art such as RT-PCR, 5' or 3' RACE to directly measure the expression levels of 19.5 and/or 19.5-like polypeptides. RNA also can be isolated and probed directly such as by solution hybridization or indirectly by hybridization to immobilized RNA. Similarly, when determining the expression level of 19.5 and/or 19.5-like polypeptides using polypeptide detection or enzyme activity formats, lysates can be assayed directly, or they can be further fractionated to enrich for the inventive polypeptides and their corresponding activities. Numerous other methods applicable for use with various cell fractions are well known to those skilled in the art and can accordingly be used in the methods of the invention.

The sample (such as a skin sample) can be obtained directly from the individual or, alternatively, it can be obtained from other sources for testing. Similarly, the sample can be tested when it is freshly isolated or it can be tested following short or prolonged periods of cryopreservation without substantial loss in accuracy or sensitivity. If the sample is to be tested following an indeterminate period of time, it can be obtained and then cryopreserved, or stored at 4° C. for short periods of time, for example. An advantage of the diagnostic methods of the invention is that they do not require histological analysis of the sample. As such, the sample can be initially disaggregated, lysed, fractionated or purified and the active component stored for later diagnosis.

The diagnostic methods of the invention are applicable for use with a variety of different types of samples other than skin cell samples. For example, intracellular 19.5 and/or 19.5-like polypeptides, and/or nucleic acid molecules encoding 19.5 and/or 19.5-like polypeptides, may leak into the extracellular space when a psoriatic condition causes a disruption of the normal skin architecture. Therefore, the diagnostic methods of the invention are applicable with fluid samples collected from an individual having, or suspected of having psoriasis.

Fluid samples which can be measured for 19.5 and/or 19.5-like polypeptides expression, levels include, for example, blood, serum, lymph, urine and semen. Other bodily fluids are known to those skilled in the art and are similarly applicable for use as a sample in the diagnostic methods of the invention. One advantage of analyzing fluid samples is that they are readily obtainable, in sufficient quantity, without invasive procedures as required by biopsy and surgery. Analysis of fluid samples such as blood, serum and urine will generally be in the diagnostic formats described above and below which measure 19.5 and/or 19.5-like polypeptide levels or activity. As the inventive polypeptides are circulating in bodily fluids, the methods will be similar to those which measure expression levels from cell lysates, fractionated portions thereof or purified components.

Psoriasis can be diagnosed, predicted or prognosed by measuring the expression levels of 19.5 and/or 19.5-like polypeptides, and/or nucleic acid molecules encoding 19.5 and/or 19.5-like polypeptides, in a tissue or cell sample, circulating fluid, or other bodily fluid obtained from the individual. As described above, expression levels can be measured by a variety methods known in the art. For example, the expression level of a nucleic acid molecule encoding a 19.5 and/or 19.5-like polypeptide can be determined by measuring the amount of a 19.5 and/or 19.5-like RNA or polypeptide in a sample from the individual.

Given the teachings and guidance provided herein, the choice of measuring nucleic acid (such as RNA), polypeptide or activity will be that of the user. Considerations such as the sample type, availability and amount will also influence selection of a particular diagnostic format. For example, if the sample is a keratinocyte cell sample and there is only a small amount available, then diagnostic formats which measure the amount of RNA by, for example, PCR amplification, can be an appropriate choice for determining the expression level of a nucleic acid molecule of the invention. Alternatively, if the sample is a blood sample and the user is analyzing numerous different samples simultaneously, such as in a clinical setting, then a multi sample format, such as an Enzyme Linked Immunoabsorbant Assay (ELISA), which measures the amount of polypeptide can be an appropriate choice for determining the expression level of a polypeptide of the invention. Additionally, nucleic acid molecules released into bodily fluids from psoriatic skin cells can also be analyzed by, for example, PCR or RT-PCR. Those skilled in the art will know, or can determine, which format is amenable for a particular application and which methods or modifications known within the art are compatible with a particular type of format.

Hybridization methods are applicable for measuring the amount of RNA as an indicator of expression levels. There are numerous methods well known in the art for detecting nucleic acid molecules by specific or selective hybridization with a complementary probe. Such methods include both solution hybridization procedures and solid-phase hybridization procedures where the probe or sample is immobilized to a solid support. Descriptions for such methods can be found in, for example, Sambrook et al., supra, and in Ausubel et al., supra. Specific examples of such methods include PCR and other amplification methods such as RT-PCR, 5' or 3' RACE, RNase protection, RNA blot, dot blot or other membrane-based technologies, dip stick, pin, ELISA or two-dimensional arrays immobilized onto chips as a solid support. These methods can be performed using either qualitative or quantitative measurements, all of which are well known to those skilled in the art.

PCR or RT-PCR can be used with isolated RNA or crude cell lysate preparations. As described previously, PCR is advantageous when there is little starting material. A further description of PCR methods can be found in, for example, Dieffenbach, C. W., and Dveksler, G. S., *PCR Primer: A Laboratory Manual*, Cold Spring Harbor Press, Plainsview, N.Y. (1995). Multi sample formats such as an ELISA or two-dimensional array offer the advantage of analyzing numerous, different samples in a single assay. A particular example of a two-dimensional array used in a hybridization format is described further below in the Examples. In contrast, solid-phase dip stick-based methods offer the advantage of being able to rapidly analyze a patient's fluid sample and obtain an immediate result.

Polynucleotide probes useful for measuring the expression level of nucleic acid molecules encoding 19.5 and/or 19.5-like polypeptides by hybridization include, for example, all of the inventive nucleic acid molecules described herein. Briefly, for detection by hybridization, the polynucleotide probes of the invention having detectable labels are added to a cell, tissue or fluid sample obtained from an individual under conditions which allow annealing of the probe to RNA. Such conditions are well known in the art for both solution and solid phase hybridization procedures. Moreover, optimization of hybridization conditions can be performed, if desired, by hybridization of an aliquot of the sample at different temperatures, durations and in different buffer conditions. Such procedures are routine and well known to those skilled. Following annealing, the sample is washed and the signal is measured and compared with a suitable control or standard value. The magnitude of the hybridization signal is directly proportional to the expression levels of the polynucleotide for which the probe is specific.

A suitable control for comparison can be, for example, the expression level of a nucleic acid molecule encoding a 19.5 or 19.5-like polypeptide from a skin cell or a fluid sample obtained from a normal individual. The control sample for comparison can be measured simultaneously with one or more test samples or, alternatively, expression levels can be established for a particular type of sample and standardized to internal or external parameters such as polypeptide or polynucleotide content, cell number or mass of tissue. Such standardized control samples can then be directly compared with results obtained from the test sample. An increase (such as, by way of non-limiting example, an increase of two-fold or more) of expression levels of a nucleic acid molecule encoding a 19.5 or 19.5-like polypeptide indicates the presence of psoriasis in the tested individual.

The diagnostic procedures described above and below can additionally be used in conjunction with other psoriasis markers, for simultaneous or independent corroboration of a sample. Those skilled in the art will know which markers are applicable for use in conjunction with a nucleic acid molecule or polypeptide of the invention to delineate more specific diagnostic information such as that described above.

Therefore, in one aspect, the invention provides a method of diagnosing or predicting the susceptibility of a psoriatic condition in an individual suspected of having psoriasis where the expression level of a nucleic acid molecule of the invention is determined by measuring the amount of its respective RNA. The amount of 19.5 or 19.5-like RNA can be determined by hybridization with a polynucleotide probe of at least 10 nucleotides in length.

In those embodiments of the methods of the invention wherein susceptibility to psoriasis in an individual is diagnosed by measuring the amount of 19.5 and/or 19.5-like polypeptide, essentially all modes of affinity binding assays are applicable for use in determining the amount of polypeptide in a sample. Such methods are rapid, efficient and sensitive. Moreover, affinity binding methods are simple and can be adjusted to be performed in a variety of clinical settings and under conditions to suit a variety of particular needs. Affinity binding assays which are known and can be used in the methods of the invention include both soluble and solid phase formats. A specific, representative, example of a soluble phase affinity binding assay is immunoprecipitation using an antibody selective for 19.5 or 19.5-like polypeptide. Solid phase formats are advantageous for the methods of the invention since they are rapid and can be performed more easily on multiple different samples simultaneously without losing sensitivity or accuracy. Moreover, solid phase affinity binding assays are further amenable to high throughput screening and automation.

Specific examples of solid phase affinity binding assays include immunoaffinity binding assays such as an ELISA and radioimmune assay (RIA). Other solid phase affinity binding assays are known to those skilled in the art and are applicable to the methods of the invention. Although affinity binding assays are generally formatted for use with an antibody that is selective for the analyte or ligand of interest, essentially any binding agent can be alternatively substituted for selectively binding the antibody. Such binding agents include, for example, macromolecules such as polypeptides, peptides, nucleic acids, lipids and sugars as well as small molecule compounds. Methods are known in the art for identifying such molecules which bind selectively to a particular analyte or ligand and include, for example, combinatorial libraries. Thus, for a molecule other than an antibody to be used in an affinity binding assay, all that is necessary is for the binding agent to exhibit selective binding activity for the inventive polypeptide.

Various modes of affinity binding formats are similarly known which can be used in the diagnostic methods of the invention. For the purpose of illustration, particular embodiments of such affinity binding assays will be described further in reference to immunoaffinity binding assays. The various modes of affinity binding assays, such as immunoaffinity binding assays, include for example, solid phase ELISA and MA as well as modifications thereof. Such modifications thereof include, for example, capture assays and sandwich assays as well as the use of either mode in combination with a competition assay format. The choice of which mode or format of immunoaffinity binding assay to use will depend on the intent of the user. Such methods can be found described in common laboratory manuals such as Harlow and Lane, *Using Antibodies: A Laboratory Manual*, Cold Spring Harbor Laboratory Press, New York (1999).

As with the hybridization methods described previously, the diagnostic formats employing affinity binding can be used in conjunction with a variety of detection labels and systems known in the art to quantitate amounts of a polypeptide in the analyzed sample. Detection systems include the detection of bound polypeptide by both direct and indirect means. Direct detection methods include labeling of an antibody or binding agent that binds specifically to a 19.5 or 19.5-like polypeptide. Indirect detection systems include, for example, the use of labeled secondary antibodies and binding agents.

Secondary antibodies, labels and detection systems are well known in the art and can be obtained commercially or by techniques well known in the art. The detectable labels and systems employed with a binding agent that is specific to a 19.5 or 19.5-like polypeptide should not impair binding of the agent to its cognate inventive polypeptide. Moreover, multiple antibody and label systems can be employed for detecting bound antigen/antibody complexes to enhance the sensitivity of the binding assay if desired.

As with the hybridization formats described previously, detectable labels can be essentially any label that can be quantitated or measured by analytical methods. Such labels include, for example, enzymes, radioisotopes, fluorochromes as well as chemi- and bioluminescent compounds. Specific examples of enzyme labels include horseradish peroxidase (HRP), alkaline phosphatase (AP), 3-galactosidase, urease and luciferase.

A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). Luciferin is the substrate compound for luciferase which emits light following ATP-dependent oxidation.

Fluorochrome detection labels are rendered detectable through the emission of light of ultraviolet or visible wavelength after excitation by light or another energy source. DAPI, fluorescein, Hoechst 33258, R-phycocyanin, B-phycoerythrin, R-phycoerythrin, rhodamine, Texas red and lissamine are specific examples of fluorochrome detection labels that can be utilized in the affinity binding formats of the invention. Particularly useful fluorochromes include fluorescein and rhodamine.

Chemiluminescent as well as bioluminescent detection labels are convenient for sensitive, non-radioactive detection of 19.5 or 19.5-like polypeptides, and nucleic acid molecules encoding 19.5 or 19.5-like polypeptides, and can be obtained commercially from various sources such as Amersham Lifesciences, Inc. (Arlington Heights, Ill.).

Radioisotopes can alternatively, be used as detectable labels for use in the binding assays of the invention. Iodine-125 is a specific example of a radioisotope useful for a detectable label.

Signals from detectable labels can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis of the amount of bound agent can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The invention further provides a method of identifying a compound that inhibits the activity of a 19.5 or 19.5-like polypeptide. The methods consist of contacting a sample containing a 19.5 or 19.5-like polypeptide and an appropriate substrate, with a test compound under conditions that allow product formation from the substrate, and measuring the amount of the product formation from the substrate. A decrease in the amount of product formation from the polypeptide substrate in the presence of the test compound compared to the absence of the test compound indicates that the compound has inhibitory activity towards the polypeptide activity. Similarly, compounds that increase the activity of a 19.5 or 19.5-like polypeptide also can be identified. A test compound added to a sample containing a 19.5 or 19.5-like polypeptide and an appropriate substrate which increases the amount of product or rate of product formation or chemical modification of the substrate, compared to the absence of the test compound, indicates that the compound increases the activity of the polypeptide. Therefore, in one aspect, the invention provides a method of identifying compounds that modulate the activity of 19.5 or 19.5-like polypeptides. The polypeptide containing sample used for such a method can be serum, skin tissue, a keratinocyte cell population or a recombinant cell population expressing a 19.5 and/or 19.5-like polypeptide.

The methods for determining the activity of a 19.5 or 19.5-like polypeptide in a sample described above can also be adapted for screening test compounds to determine their ability to inhibit or increase the enzymatic and/or biological activity of a 19.5 or 19.5-like polypeptide. In such cases, a test compound is added to a reaction system and the effect of the test compound on production of product is observed. Those compounds which inhibit the product formation or rate of product formation are considered as potential antagonists of the 19.5 or 19.5-like polypeptides and further as potential therapeutic agents for treatment of psoriasis. Similarly, those compounds which increase the product or rate of product formation are considered as potential agonists of the 19.5 or 19.5-like polypeptides and further as potential therapeutic agents for the treatment of psoriasis.

A reaction system for identifying a compound that inhibits or enhances the activity of 19.5 or 19.5-like polypeptides can be performed using essentially any source of 19.5 or 19.5-like polypeptide activity. Such sources include, for example, a skin cell sample, lysate or fractionated portion thereof; a bodily fluid such as blood, serum or urine from an individual with psoriasis; a recombinant cell or soluble recombinant source, and an in vitro translated source. The source of 19.5 or 19.5-like polypeptide is combined with an appropriate substrate as described above and incubated in the presence or absence of a test inhibitory compound. The reaction rate or extent of the usage of the substrate in the presence of the test compound is compared with that in the absence of the test compound. Inhibitors of 19.5 or 19.5-like polypeptides identified in this way can then be subjected to further in vitro or in vivo testing to confirm that they inhibit the production of substrates of 19.5 or 19.5-like polypeptides in cellular and animal models.

Suitable test compounds for the inhibition or enhancement assays can be any substance, molecule, compound, mixture of molecules or compounds, or any other composition which is suspected of being capable of inhibiting 19.5 or 19.5-like polypeptide activity in vivo or in vitro. The test compounds can be heterocyclic organic compounds such as steroids or steroid derivatives, macromolecules, such as biological polymers, including proteins, polysaccharides and nucleic acids. Sources of test compounds which can be screened for inhibitory activity against 19.5 or 19.5-like polypeptides include, for example, libraries, of peptides, polypeptides, DNA, RNA and small organic compounds. Additionally, test compounds can be preselected based on a variety of criteria. For example, suitable test compounds can be selected, for example, randomly and tested by the screening methods of the present invention. Test compounds are typically administered to the reaction system at a concentration in the range from about 1 nM to 1 mM. Useful test compounds such as steroids and steroid derivatives are typically lipophilic, thus allowing them to cross the cell membrane. In addition, routine ligand specific targeting methods are useful for testing compounds for inhibitory activity.

Thus, in another aspect, the present invention provides methods for ameliorating the symptoms and/or progression of psoriasis, the methods comprising administering to an individual suffering from psoriasis an inhibitory amount of a selective inhibitor (such as an antisense nucleic acid molecule or an antibody) of at least one polypeptide chosen from the group consisting of 19.5 and 19.5-like, wherein the inhibitory amount causes a reduction (such as, by way of non-limiting example, a reduction of about 2-fold) in the amount and/or activity of the chosen polypeptide(s).

Such inhibitors may be produced using methods which are generally known in the art, and include the use of purified 19.5 or 19.5-like polypeptide to produce antibodies or to screen libraries of compounds, as described previously, for those which specifically bind to 19.5 or 19.5-like polypeptide. Lipophilic compounds able to cross the lipid bilayer that makes up cell membranes are especially useful inhibitors for practicing the methods of the invention.

One embodiment of the present invention relates to an antibody or antigen binding fragment that selectively binds to a protein of the present invention. Such an antibody can selectively bind to any of the proteins described herein, including fragments and other homologues of such receptors. According to the present invention the phrase "selectively binds to" refers to the ability of an antibody, antigen binding fragment or binding partner of the present invention to preferentially bind to specified proteins (e.g., a PS receptor of the present invention). More specifically, the phrase "selectively binds" refers to the specific binding of one protein to another (e.g. an antibody, fragment thereof or binding partner to an antigen), wherein the level of binding as measured by any standard assay (e.g. immunoassay), is statistically significantly higher than the background control for the assay. For example, when performing an immunoassay, controls typically include a reaction well/tube that contain antibody or antigen binding fragment alone (i.e. in the absence of antigen), wherein the amount of reactivity (e.g. non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.

Antibodies are characterized in that they comprise immunoglobulin domains, and as such they are members of the immunoglobulin superfamily of proteins Generally speaking an antibody molecule comprises two types of chain. One type of chain is referred to as the heavy or H chain and the other is referred to as the light or L chain. The two chains are present in an equimolar ratio, with each antibody molecule typically having two H chains and two L chains. The two H chains are linked together by disulfide bonds and each H chain is linked to an L chain by a disulfide bond. There are only two types of L chains referred to as lambda ($\lambda$) and kappa ($\kappa$) chains. In contrast there are five major H chain classes referred to as isotypes. The five classes include immunoglobulin M (IgM or $\mu$), immunoglobulin D (IgD or $\delta$), immunoglobulin G (IgG or $\gamma$), immunoglobulin A (IgA or $\alpha$), immunoglobulin E (IgE or $\epsilon$). The distinctive characteristics between such isotypes are defined by the constant domain of the immunoglobulin and are discussed in detail below. Human immunoglobulin molecules comprise nine isotypes, IgM, IgD, IgE, four classes of IgG including IgG1 ($\gamma$1), IgG2 ($\gamma$2), IgG3 ($\gamma$3) and IgG4 ($\gamma$4), and two subclasses of IgA, including IgA1 ($\alpha$1) and IgA2 ($\alpha$2).

Each H or L chain of an immunoglobulin molecule comprises two regions referred to as L chain variable domains ($V_L$ domains) and L chain constant domains ($C_L$ domains), and H chain variable domains ($V_H$ domains) and H chain constant domains ($C_H$ domains). A complete CH domain comprises 3 sub-domains (CH1, CH2, CH3) and a hinge region. Together, one H chain and one L chain can form an arm of an immunoglobulin molecule having an immunoglobulin variable region. A complete immunoglobulin molecule comprises two associated (e.g. di-sulfide linked) arms. Thus, each arm of a whole immunoglobulin comprises a $V_{H+L}$ region, and a $C_{H+L}$ region. As used herein, the term variable region or V region refers to a $V_{H+L}$ region (also known as an Fv fragment), a $V_L$ region or a $V_H$ region. As used herein, the term "constant region" or "C region" refers to a $C_{H+L}$ region, a $C_L$ region or a $C_H$ region.

Limited digestion of an immunoglobulin with a protease may produce two fragments. An antigen binding fragment is referred to as a Fab, Fab' or a F(ab')$_2$ fragment. A fragment lacking the ability to bind to antigen is referred to as an Fc fragment. A Fab fragment comprises one arm of an immunoglobulin molecule containing a L chain ($V_L+C_L$ domains) paired with the $V_H$ region and a portion of the $C_H$ region (CH1 domain). A Fab' fragment corresponds to a Fab fragment with part of the hinge region attached to the CH1 domain. An F(ab')$_2$ fragment corresponds to two Fab' fragments that are normally covalently linked to each other through a di-sulfide bond, typically in the hinge regions).

The $C_H$ domain defines the isotype of an immunoglobulin and confers different functional characteristics depending upon the isotype. For example μ constant regions enable the formation of pentameric aggregates of IgM molecules and cc constant regions enable the formation of dimers.

The antigen specificity of an immunoglobulin molecule is conferred by the amino acid sequence of a variable, or V, region. As such V regions of different immunoglobulin molecules can vary significantly depending upon their antigen specificity. Certain portions of a V region are more conserved than others and are referred to as framework regions (FW regions). In contrast, certain portions of a V region are highly variable and are designated hypervariable regions. When the $V_L$ and $V_H$ domains pair in an immunoglobulin molecule, the hypervariable regions from each domain associate and create hypervariable loops that form the antigen binding site. Thus, the hypervariable loops determine the specificity of an immunoglobulin and are termed complementarity-determining regions (CDRs) because their surfaces are complementary to antigens.

Further variability of V regions is conferred by combinatorial variability of gene segments that encode an immunoglobulin V region. Immunoglobulin genes comprise multiple germline gene segments which somatically rearrange to form a rearranged immunoglobulin gene that encodes an immunoglobulin molecule. VL regions are encoded by a L chain V gene segment and J gene segment (joining segment). VH regions are encoded by a H chain V gene segment, D gene segment (diversity segment) and J gene segment (joining segment).

Both an L chain and H chain V gene segment contains three regions of substantial amino acid sequence variability. Such regions are referred to as L chain CDR1, CDR2, and CDR3, and H chain CDR1, CDR2, and CDR3 respectively. The length of an L chain CDR1 can vary substantially between different $V_L$ regions. For example, the length of CDR1 can vary from about 7 amino acids to about 17 amino acids. In contrast the lengths of L chain CDR2 and CDR3, typically do not vary between different $V_L$ regions. The length of an H chain CDR3 can vary substantially between different $V_H$ regions. For example, the length of CDR3 can vary from about 1 amino acid to about 20 amino acids. Each H and L chain CDR region is flanked by FW regions.

Other functional aspects of an immunoglobulin molecule include the valency of an immunoglobulin molecule, the affinity of an immunoglobulin molecule, and the avidity of an immunoglobulin molecule. As used herein, affinity refers to the strength with which an immunoglobulin binds to an antigen at a single site on a immunoglobulin molecule (i.e., a monovalent Fab fragment binding to a monovalent antigen). Affinity differs from avidity which refers to the sum total of the strength with which an immunoglobulin binds an antigen. Immunoglobulin binding affinity can be measured using techniques standard in the art, such as competitive binding techniques, equilibrium dialysis or BIAcore methods. As used herein, valency refers to the number of different antigen binding sites per immunoglobulin molecule (i.e. the number of antigen binding sites per antibody molecule of antigen binding fragment). For example a monovalent immunoglobulin molecule can bind to one antigen at one time, whereas a bivalent immunoglobulin molecule can bind to two or more antigens at one time, and so forth. Both monovalent and bivalent antibodies that selectively bind to PS receptors of the present invention are encompassed herein.

In one embodiment of the present invention, a monovalent antibody can be used as a regulatory compound. Divalent antibodies can also be used in the present invention.

Isolated antibodies of the present invention can include serum containing such antibodies, or antibodies that have been purified to varying degrees. Whole antibodies of the present invention can be polyclonal or monoclonal. Alternatively functional equivalents of whole antibodies, such as antigen binding fragments in which one or more antibody domains are truncated or absent (e.g. Fv, Fab, Fab' or F(ab')$_2$ fragments) as well as genetically engineered antibodies or antigen binding fragments thereof, including single chain antibodies or antibodies that can bind to more than one epitope (e.g., bi-specific antibodies), or antibodies that can bind to one or more different antigen (i.e., bi- or multi-specific antibodies), may also be employed in the invention Generally, in the production of an antibody, a suitable experimental animal, such as, for example, but not limited to, a rabbit, sheep, hamster, guinea pig, mouse rat, or chicken, is exposed to an antigen against which an antibody is desired. Typically, an animal is immunized with an effective amount of antigen that is injected into the animal. The animal's immune system is then allowed to respond over a period of time. The immunization process can be repeated until the immune system is found to be producing antibodies to the antigen. In order to obtain polyclonal antibodies specific for the antigen, serum is collected from the animal that contains the desired antibodies) or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies, may be produced according to the methodology of Kohler & Milstein (*Nature,* 1975 256:495-497) for example, B lymphocytes are recovered from the spleen (or from any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

In one embodiment, the antibody is a bi- or multi-specific antibody. A bi-specific (or multi-specific) antibody is capable of binding two (or more) antigens, as with a divalent (or multivalent) antibody, but in this case, the antigens are different antigens (i.e., the antibody exhibits dual or greater specificity). A bi-specific antibody suitable for use in the present method includes an antibody having: (a) a first portion (e.g., a first antigen binding portion) which binds to 19.5 or 19.5 like; and (b) a second portion which binds to a cell surface molecule expressed by a cell which expresses a 19.5 or 19.5- like. In this embodiment, the second portion can bind to any cell surface molecule. In a preferred embodiment, the second portion is capable of targeting the regulatory antibody to a specific target cell (i.e., the regulatory antibody binds to a target molecule). For example, the second portion of the bi-specific antibody can be an antibody that binds to another cell surface molecule on a target cell, such as a macrophage, a fibroblast, or an epithelial cell, for example.

A preferred method to produce antibodies of the present invention includes: (a) administering to an animal an effective amount of a protein, peptide or mimetic thereof of the present invention to produce antibodies; and (b) recovering the antibodies. In another method, antibodies of the present invention are produced recombinantly. For example, once a cell line, for example a hybridoma, expressing an antibody according to the invention has been obtained it is possible to clone therefrom the cDNA and to identify the variable region genes encoding the desired antibody, including the sequences encoding the CDRs. From here, antibodies and antigen binding fragments according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming/transfecting an appropriate host cell, in which production of the antibody will occur. Suitable expression hosts include bacteria, (for example, an *E. coli* strain), fungi, (in particular yeasts, e.g. members of the genera *Pichia, Saccharomyces*, or *Kluyveromyces*,) and mammalian cell lines, e.g., a non-producing myeloma cell line, such as a mouse NSO line, or CHO cells. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al. [*Molecular Cloning*, Cold Spring Harbor Laboratory, New York, 1989]; DNA sequencing can be performed as described in Sanger et al. [*PNAS* 74:5463, (1977)] and the Amersham International Plc. sequencing handbook; and site directed mutagenesis can be carried out according to the method of Kramer et al. [*Nucl. Acids Res.* 12:9441, (1984)] and the Anglian Biotechnology Ltd. handbook. Additionally, there are numerous publications, including patent specifications, detailing techniques suitable for the preparation of antibodies by manipulation of DNA, creation of expression vectors and transformation of appropriate cells, for example as reviewed by Mountain, A. and J. R. Adair in *Biotechnology and Genetic Engineering Reviews [ed. Tombs, M. P., 10*, Chapter 1, 1992, Intercept, Andover, UK] and in the aforementioned European Patent Applications.

Alternative methods, employing, for example, phage display technology (see, for example U.S. Pat. Nos. 5,969,108, 5,565,332, 5,871,907, and 5858657) or the selected lymphocyte antibody method of U.S. Pat. No. 5,627,052 may also be used for the production of antibodies and/or antigen fragments of the invention, as will be readily apparent to the skilled individual.

Antibodies raised against defined proteins can be advantageous because such antibodies are not substantially contaminated with antibodies against other substances that might otherwise cause interference in a diagnostic assay or side effects if use in a therapeutic composition.

The invention also extends to non-antibody polypeptides, sometimes referred to as binding partners, that have been designed to bind specifically to, and either activate or inhibit as appropriate, a PS receptor of the invention. Examples of the design of such polypeptides, which possess a prescribed ligand specificity are given in Beste et al. (1999, *Proceedings of the National Academy of Science* 96:1898-1903).

Genetically engineered antibodies of the invention include those produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications EP-A 0194276, EP-A 0239400, EP-A 0451216 and EP-A 0460617.

It is presently preferred that antibodies of the present invention are CDR-grafted antibodies. The term "CDR-grafted antibody" as used herein refers to an antibody molecule wherein the heavy and/or light chain contains one or more CDRs from a donor antibody (e.g., a murine monoclonal antibody) grafted into a heavy and/or light chain variable region framework of an acceptor antibody (e.g., human antibody). Construction of CDR-grafted antibodies is fully described in European Patent Application EP-A-0239400, which publication is incorporated herein by reference.

In another embodiment, 19.5 and 19.5-like polypeptides can be utilized in ligand based discovery or chemical genomics approach to find additional members of a specific pathway. Examples of chemical genomics include *Nature Reviews, Genetics,* 1:117, November 2000; *Nature Biotechnology* 18:304, March 2000; and *J. Org. Chem.,* 1997, 62:2823-2831.

In one embodiment of the invention, nucleic acid molecules encoding a 19.5 or 19.5-like polypeptide, or nucleic acid molecules complementary to all or part of one or more nucleic acid molecule encoding a 19.5 or 19.5-like polypeptide, or any fragment thereof, can be used for therapeutic purposes. In one aspect, antisense molecules to nucleic acid molecules encoding a 19.5 or 19.5-like polypeptide can be used to block the transcription or translation of an mRNA homologous to the antisense molecule. Specifically, one or more nucleic acid molecules complementary to any portion of an mRNA transcript encoding a 19.5 or 19.5-like polypeptide are introduced into cells. Such methods are well known in the art, and sense or antisense oligonucleotides or larger polynucleotide fragments, can be designed from various locations along the coding or control regions of sequences encoding a 19.5 or 19.5-like polypeptide. Thus, antisense molecules may be used to modulate the activity of 19.5 and/or 19.5-like polypeptides, or to achieve regulation of gene function.

Expression vectors derived, for example, from retroviruses, adenovirus, adeno-associated virus (AAV), herpes or vaccinia viruses, or from various bacterial plasmids can be used for delivery of antisense nucleotide sequences to a skin cell population. The viral vector selected should be able to infect the skin cells and be safe to the host and cause minimal cell transformation. Retroviral vectors and adenoviruses offer an efficient, useful, and well characterized means of introducing and expressing foreign genes efficiently in mammalian cells. These vectors are well known in the art and have very broad host and cell type ranges, express genes stably and efficiently. Methods which are well known to those skilled in the art can be used to construct such recombinant vectors and are described in Sambrook et al. (supra). Even in the absence of integration into the DNA, such vectors can continue to transcribe RNA molecules for a substantial period of time. Transient expression can last for a month or more with a non-replicating vector and even longer if appropriate replication elements are part of the vector system.

Ribozymes, enzymatic RNA molecules, can also be used to catalyze the specific cleavage of mRNAs encoding a 19.5 or 19.5-like polypeptide. The mechanism of ribozyme action involves sequence-specific hybridization of the ribozyme molecule to a complementary target RNA, followed by endonucleolytic cleavage. Specific ribozyme cleavage sites within any potential RNA target are identified by scanning the target RNA for ribozyme cleavage sites which include, for example, the following sequences: GUA, GUU, and GUC. Once identified, short RNA sequences of between 10 and 20 ribonucleotides corresponding to the region of the target polynucleotide containing the cleavage site can be evaluated for secondary structural features which can render the oligonucleotide inoperable. The suitability of candidate targets can also be evaluated by testing accessibility to hybridization with complementary oligonucleotides using ribonuclease protection assays. Antisense molecules and ribozymes can be prepared by any method known in the art for the synthesis of nucleic acid molecules.

In another embodiment, the 19.5 gene promoter and regulatory regions can be used for constructing vectors for psoriasis therapy. The promoter and regulatory regions can be operatively fused to a therapeutic polynucleotide for keratinocyte specific expression. This method can include the addition of one or more enhancer elements which amplify expression of the heterologous therapeutic polynucleotide without compromising tissue specificity.

It is understood that modifications which do not substantially affect the activity of the various embodiments of this invention are also included within the definition of the invention provided herein. Accordingly, the following examples are intended to illustrate but not limit the present invention.

Example 1

Expression Profile of 19.5 and 19.5-Like mRNA Molecules in Human Tissues

To test what tissues expressed human 19.5 gene, PCR was used to examine cDNA prepared from mRNA transcripts isolated from thirty-two (32) different human tissues. All tissues were purchased from commercial sources Invitrogen, (Carlsbad, Calif.), Colette, (Palo Alto, Calif.). Biochain (Hayward, Calif.), except for PBL (peripheral blood lymphocytes) and bone which were prepared in-house. The tissue sources assayed are: heart, small intestine, mammary gland, spleen, prostate, stomach, skeletal muscle, thymus, skin, uterus, kidney bone marrow, liver, colon, lung, trachea, pancreas, brain, salivary gland, cerebellum, thyroid, fetal brain, parotid, fetal liver, umbilical cord, spinal cord, ovary, placenta, PBL, adrenal gland, and bone.

cDNA was prepared from 5 μg of total RNA using an oligo dT primer and standard reverse transcription methods according to manufacturers protocols. (Gibco BRL Cat No. 18089-011, Frohman, 1985).

15 ng/μl aliquots of each cDNA sample were subjected to PCR amplification using primers [CCACTCAATGC-GAGACGTGGCCAGATCC] (SEQ ID NO:5) and [CCCAG-TAACCTTGAGCATATCTATAAGGC] (SEQ ID NO:6). PCR cycling conditions were 94° C. 10 s, 62° C. 30 s, 72° C. 90 sec for 35 cycles. The resulting amplified DNA products were separated using gel electrophoresis and according to this analysis, 19.5 gene is readily detected in only the normal skin and fetal skin cDNA samples, although lower expression levels can be seen in other tissues such as testis, uterus, lung, salivary gland, parotid adipose tissue and cartilage.

To test what tissues expressed human 19.5-like gene, PCR was used to examine cDNA prepared from mRNA transcripts isolated from thirty-two (32) different human tissues. All tissues were purchased from commercial sources (Invitrogen, Carlsbad, Calif.), Clontech, (Palo Alto, Calif.). Biochain (Hayward, Calif.), except for PBL (peripheral blood lymphocytes) and bone which were prepared in-house. The tissue sources assayed were: heart, small intestine, mammary gland, spleen, prostate, stomach, skeletal muscle, thymus, skin, uterus, kidney bone marrow, liver, colon, lung, trachea, pancreas, brain, salivary gland, cerebellum, thyroid, fetal brain, parotid, fetal liver, umbilical cord, spinal cord, ovary, placenta, PBL, adrenal gland, and bone.

cDNA was prepared from 5 μg of total RNA using an oligo dT primer and standard reverse transcription methods according to manufacturers protocols. (Gibco BRL Cat No. 18089-011, Frohman, 1985).

15 ng/μl aliquots of each cDNA sample were subjected to PCR amplification using primers [GCCTCCGCTGGAC-CAGCACATC] (SEQ ID NO:7) and [GACATCTGCGC-CCTCCGCATCTC] (SEQ ID NO:8). PCR cycling conditions were 94° C. 10 s, 62° C. 30 s, 72° C. 90 sec for 35 cycles. The resulting amplified DNA products were separated using gel electrophoresis and showed expression in gastrointestinal tissues including colon, small intestine and stomach (the expression in stomach is lower), however lower signals were also seen in trachea, salivary gland and parotid.

Example 2

Production of Antibodies Specific to 19.5 or 19.5-Like Polypeptides

Antibodies that specifically bind to 19.5 or 19.5-like polypeptides can be prepared by a variety of methods. For example, 19.5 or 19.5-like polypeptide is administered to an animal to induce the production of sera containing polyclonal antibodies. In one method, a preparation of the secreted protein is prepared and purified to render it substantially free of natural contaminants. Such a preparation is then introduced into an animal in order to produce polyclonal antisera of greater specific activity.

In another method, antibodies that specifically bind to 19.5 or 19.5-like polypeptides are monoclonal antibodies (or protein binding fragments thereof). Such monoclonal antibodies can be prepared using hybridoma technology. (Köhler et al., *Nature* 256:495, 1975; Köhler et al., *Eur. J. Immunol.* 6:511, 1976; Köhler et al., *Eur. J. Immunol.* 6:292, 1976; Hammerling et al., in: *Monoclonal Antibodies and T-Cell Hybridomas*, Elsevier, N.Y., pp. 563-681 (1981)). In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed; however, it is preferable to employ the parent myeloma cell line (SP20), available from the ATCC. After fusion, the resulting hybridoma cells are selectively maintained in HAT medium, and then cloned by limiting dilution as described by Wands et al. (*Gastroenterology* 80:225, 1981). The hybridoma cells obtained through such a selection are then assayed to identify clones which secrete antibodies capable of binding to 19.5 or 19.5-like polypeptides.

Alternatively, antibodies capable of binding to 19.5 or 19.5-like polypeptides can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, *Science* 229:1202, 1985; Oi et al., *BioTechniques* 4:214, 1986; Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643, 1984; Neuberger et al., *Nature* 314:268, 1985).

In some embodiments, for in vivo use of antibodies in humans, the antibody can be modified by attachment of polyethylene glycol (PEG) to extend the lifetime of the antibody.

Example 3

Method of Detecting Abnormal Levels of 19.5 and/or 19.5-Like Polypeptide in a Biological Sample 19.5 and/or 19.5-like polypeptides can be detected in a biological sample according to the following representative example. Methods of detection are numerous, and thus it is understood that one skilled in the art can modify the following assay to fit their particular needs.

Antibody-sandwich ELISAs are used to detect 19.5 and/or 19.5-like polypeptides in a sample, preferably a biological sample. Wells of a microtiter plate are coated with specific antibodies, at final concentration typically in the range of 0.2 to 10 µg/ml. The antibodies can be monoclonal or polyclonal and are produced, for example, by the methods described supra. The wells are blocked so that non-specific binding of the polypeptide to the well is reduced.

The coated wells are then incubated for >2 hours at room temperature with a sample containing the 19.5 and/or 19.5-like polypeptide. Preferably, serial dilutions of the sample should be used to validate results. The plates are then washed three times with deionized or distilled water to remove unbound 19.5 and/or 19.5-like polypeptide.

Next, 50 µl of specific antibody-alkaline phosphatase conjugate, at a concentration of 25-400 ng, is added and incubated for 2 hours at room temperature. The plates are again washed three times with deionized or distilled water to remove unbounded conjugate.

Add 75 µl of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot 19.5 and/or 19.5-like polypeptide concentration on the X-axis (log scale) and fluorescence or absorbance on the Y-axis (linear scale). Interpolate the concentration of the 19.5 and/or 19.5-like polypeptide in the sample using the standard curve.

Example 4

Method of Treating Increased Levels of 19.5 or 19.5-Like Polypeptides in a Subject Antisense technology can be used to inhibit production of a 19.5 and/or 19.5-like polypeptide. This technology is one example of a method of decreasing levels of a 19.5 and/or 19.5-like polypeptide.

For example, a patient diagnosed with a condition, such as psoriasis, caused, at least in part, by abnormally increased levels of a 19.5 and/or 19.5-like polypeptide is administered intravenously antisense polynucleotides at 0.5, 1.0, 1.5, 2.0 and 3.0 mg/kg day for 21 days. This treatment is repeated after a 7-day rest period if the treatment was well tolerated. Antisense nucleic acid molecules useful in this aspect of the invention hybridize under stringent conditions to a portion of an mRNA molecule that encodes a 19.5 and/or 19.5-like polypeptide.

Additionally, increased levels of 19.5 and/or 19.5-like polypeptide can be treated by using an antibody that specifically binds to 19.5 and/or 19.5-like polypeptide, thereby reducing the amount of 19.5 and/or 19.5-like polypeptide within a cell.

Example 5

Method of Treating Psoriasis Using Gene Therapy

One method of treating psoriasis is gene therapy utilizing fibroblasts, which are capable of expressing a polypeptide, that are transplanted onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier et al., *DNA* 7:219, 1988), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

A cDNA encoding a 19.5 or 19.5-like polypeptide of the present invention can be amplified using PCR primers which correspond to portions of the 5' and 3' end sequences of 19.5 and 19.5-like cDNA molecules. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4. DNA ligase. The resulting mixture is maintained under conditions appropriate for ligation of the two fragments. The ligation mixture is then used to transform bacteria HB101, which are then plated onto agar containing kanamycin for the purpose of confirming that the vector has the polynucleotide of interest properly inserted.

Amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the polynucleotide is then added to the media and the packaging cells transduced with the vector. The packaging cells now produce infectious viral particles containing the polynucleotide (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

From the foregoing, it may be seen that this invention is one well-adapted to achieve all the ends and objects hereinabove set forth together with other advantages which are obvious and which are inherent to the invention. It will be understood that certain features and subcombinations are of utility and may be employed without reference to other features and subcombinations. The above examples discuss the techniques and procedures utilized and are considered to be the preferred embodiment of the current invention, and it is understood that there are many other techniques and procedures that could be employed which would allow an individual of ordinary skill in the art to perform the claimed invention. Such other techniques and procedures are contemplated by and are within the scope of the claims. Since many possible embodiments may be made of the invention without departing from the scope thereof, it is to be understood that all matter herein set forth and shown in the examples are to be interpreted as illustrative and not in a limiting sense.

Example 6

Immunohistochemistry Using Anti-19.5 Antibodies

This example describes the immunohistochemical localization of affinity-purified 19.5 antibodies to normal human skin, and also to psoriatic human skin.

Antiserum was raised in a rabbit by immunization with a peptide located close to the carboxy terminus of the human 19.5 protein. The amino acid sequence of the peptide (designated peptide C6) is CSSEVGLLKNAEREQ (SEQ ID NO:9). Antiserum raised against C6 was affinity-purified using purified C6 peptide, using standard protocols for such purification. This affinity purified C6 antisera was used at a concentration of 5 μg/ml for immunohistochemistry using standard protocols. The specificity of the immunoreactivity was confirmed by blocking the antibody binding using a preincubation of the C6 antisera with the C6 peptide (SEQ ID NO:9).

Immunohistochemistry was performed using the affinity purified C6 antiserum using sections of formaldehyde-fixed, paraffin-embedded, healthy human skin, and also psoriatic human skin. The immunohistochemistry results showed that the 19.5 protein is expressed in both normal skin and psoriatic skin. The immunohistochemistry results also showed the 19.5 protein is predominantly found in the cell membrane of keratinocytes, which is consistent with the predicted transmembrane structure of the 19.5 protein.

The immunohistochemistry results from normal skin show that the 19.5 protein is mainly present in the outermost layer of the keratinocytes in the epidermis, which is called the granular layer. The results from the psoriatic skin show that the 19.5 protein is expressed in the granular layer, and that the expression of the 19.5 protein begins earlier in the maturation of the keratinocytes (i.e., beginning in the intermediate cornified layer).

All references cited in this application are specifically incorporated in their entirety in all respects.

The embodiments of the invention in which an exclusive property or privilege is claimed are defined as follows:

1. An isolated antibody wherein said antibody binds specifically to a polypeptide consisting of the amino acid sequence set forth in SEQ ID NO:2 (19.5 polypeptide), wherein SEQ ID NO:9 (peptide C6) blocks said binding of said antibody to SEQ ID NO:2.

2. An isolated antibody of claim 1 wherein said antibody is a polyclonal antibody.

3. An isolated antibody of claim 1 wherein said antibody is a monoclonal antibody.

* * * * *

SEQUENCE LISTING

<160> NUMBER OF SEQ ID NOS: 9

<210> SEQ ID NO 1
<211> LENGTH: 1564
<212> TYPE: DNA
<213> ORGANISM: Homo Sapiens
<220> FEATURE:
<221> NAME/KEY: CDS
<222> LOCATION: (314)..(1138)

<223> OTHER INFORMATION:

<400> SEQUENCE: 1

```
gaagcacatc tggacagctg tgcggcctcc ttgcgggccg acgtcagccg agcacgtccc      60
ccacgtcctc tccttctcgc cacttattat ttattcgttt tcccaaagaa gcgactaggg     120
acccaagttt aaaaattcct ccccccactc aatgcgagac gtggccagat cccatccaac     180
acacggttta attttcatgg ggctctggga tcaaagaaac agaaacagca acaacaaaag     240
cccagccgct gtctgatttt aagctggcaa agtgggaaaa ataaagtgtt gagtaaacag     300
```

| accaagttgg atc atg ggg aat ttc aga ggt cat gcc ctc cct gga acc | 349 |
|---|---|
|            Met Gly Asn Phe Arg Gly His Ala Leu Pro Gly Thr | |
|            1          5              10 | |

| ttc ttt ttt att att ggt ctt tgg tgg tgt aca aag agt att ctg aag | 397 |
|---|---|
| Phe Phe Phe Ile Ile Gly Leu Trp Trp Cys Thr Lys Ser Ile Leu Lys | |
|        15            20           25 | |

| tat atc tgc aaa aag caa aag cga acc tgc tat ctt ggt tcc aaa aca | 445 |
|---|---|
| Tyr Ile Cys Lys Lys Gln Lys Arg Thr Cys Tyr Leu Gly Ser Lys Thr | |
|    30               35              40 | |

| tta ttc tat cga ttg gaa att ttg gag gga att aca ata gtt ggc atg | 493 |
|---|---|
| Leu Phe Tyr Arg Leu Glu Ile Leu Glu Gly Ile Thr Ile Val Gly Met | |
| 45              50              55             60 | |

| gct tta act ggc atg gct ggg gag cag ttt att cct gga ggg ccc cat | 541 |
|---|---|
| Ala Leu Thr Gly Met Ala Gly Glu Gln Phe Ile Pro Gly Gly Pro His | |
|              65              70             75 | |

| ctg atg tta tat gac tat aaa caa ggt cac tgg aat caa ctc ctg ggc | 589 |
|---|---|
| Leu Met Leu Tyr Asp Tyr Lys Gln Gly His Trp Asn Gln Leu Leu Gly | |
|            80              85             90 | |

| tgg cat cat ttc acc atg tat ttc ttc ttt ggg ctg ttg ggt gtg gca | 637 |
|---|---|
| Trp His His Phe Thr Met Tyr Phe Phe Phe Gly Leu Leu Gly Val Ala | |
|        95            100           105 | |

| gat atc tta tgt ttc acc atc agt tca ctt cct gtg tcc tta acc aag | 685 |
|---|---|
| Asp Ile Leu Cys Phe Thr Ile Ser Ser Leu Pro Val Ser Leu Thr Lys | |
|        110            115           120 | |

| tta atg ttg tca aat gcc tta ttt gtg gag gcc ttt atc ttc tac aac | 733 |
|---|---|
| Leu Met Leu Ser Asn Ala Leu Phe Val Glu Ala Phe Ile Phe Tyr Asn | |
| 125            130            135           140 | |

| cac act cat ggc cgg gaa atg ctg gac atc ttt gtg cac cag ctg ctg | 781 |
|---|---|
| His Thr His Gly Arg Glu Met Leu Asp Ile Phe Val His Gln Leu Leu | |
|               145           150           155 | |

| gtt ttg gtc gtc ttt ctg aca ggc ctc gtt gcc ttc cta gag ttc ctt | 829 |
|---|---|
| Val Leu Val Val Phe Leu Thr Gly Leu Val Ala Phe Leu Glu Phe Leu | |
|            160            165           170 | |

| gtt cgg aac aat gta ctt ctg gag cta ttg cgg tca agt ctc att ctg | 877 |
|---|---|
| Val Arg Asn Asn Val Leu Leu Glu Leu Leu Arg Ser Ser Leu Ile Leu | |
|            175            180           185 | |

| ctt cag ggg agc tgg ttc ttt cag att gga ttt gtc ctg tat ccc ccc | 925 |
|---|---|
| Leu Gln Gly Ser Trp Phe Phe Gln Ile Gly Phe Val Leu Tyr Pro Pro | |
|        190            195           200 | |

| agt gga ggt cct gca tgg gat ctg atg gat cat gaa aat att ttg ttt | 973 |
|---|---|
| Ser Gly Gly Pro Ala Trp Asp Leu Met Asp His Glu Asn Ile Leu Phe | |
| 205            210            215           220 | |

| ctc acc ata tgc ttt tgt tgg cat tat gca gta acc att gtc atc gtt | 1021 |
|---|---|
| Leu Thr Ile Cys Phe Cys Trp His Tyr Ala Val Thr Ile Val Ile Val | |
|               225           230           235 | |

| gga atg aat tat gct ttc att acc tgg ttg gtt aaa tct aga ctt aag | 1069 |
|---|---|
| Gly Met Asn Tyr Ala Phe Ile Thr Trp Leu Val Lys Ser Arg Leu Lys | |
|            240            245           250 | |

| agg ctc tgc tcc tca gaa gtt gga ctt ctg aaa aat gct gaa cga gaa | 1117 |

```
Arg Leu Cys Ser Ser Glu Val Gly Leu Leu Lys Asn Ala Glu Arg Glu
        255                 260                 265 caa gaa tca gaa gaa gaa atg tgactttgat gagcttccag tttttctaga         1168
Gln Glu Ser Glu Glu Glu Met
    270             275 taaacctttt cttttttaca ttgttcttgg ttttgtttct cgatcttttg tttggagaac    1228
agctggctaa ggatgactct aagtgtactg tttgcatttc caatttggtt aaagtatttg    1288
aatttaaata ttttctttt agctttgaaa atattttggg tgatactttc attttgcaca     1348
tcatgcacat catggtattc agggctaga gtgattttt tccagattat ctaaagttgg      1408
atgcccacac tatgaaagaa atatttgttt tatttgcctt atagatatgc tcaaggttac    1468
tgggcttgct actatttgta actccttgac catggaatta tacttgttta tcttgttgct    1528
gcaatgagaa ataaatgaat gtatgtattt tggtgc                              1564

<210> SEQ ID NO 2
<211> LENGTH: 275
<212> TYPE: PRT
<213> ORGANISM: Homo Sapiens

<400> SEQUENCE: 2

Met Gly Asn Phe Arg Gly His Ala Leu Pro Gly Thr Phe Phe Phe Ile
1               5                   10                  15

Ile Gly Leu Trp Trp Cys Thr Lys Ser Ile Leu Lys Tyr Ile Cys Lys
                20                  25                  30

Lys Gln Lys Arg Thr Cys Tyr Leu Gly Ser Lys Thr Leu Phe Tyr Arg
            35                  40                  45

Leu Glu Ile Leu Glu Gly Ile Thr Ile Val Gly Met Ala Leu Thr Gly
        50                  55                  60

Met Ala Gly Glu Gln Phe Ile Pro Gly Gly Pro His Leu Met Leu Tyr
65                  70                  75                  80

Asp Tyr Lys Gln Gly His Trp Asn Gln Leu Gly Trp His His Phe
                85                  90                  95

Thr Met Tyr Phe Phe Phe Gly Leu Leu Gly Val Ala Asp Ile Leu Cys
                100                 105                 110

Phe Thr Ile Ser Ser Leu Pro Val Ser Leu Thr Lys Leu Met Leu Ser
            115                 120                 125

Asn Ala Leu Phe Val Glu Ala Phe Ile Phe Tyr Asn His Thr His Gly
        130                 135                 140

Arg Glu Met Leu Asp Ile Phe Val His Gln Leu Val Leu Val Val
145                 150                 155                 160

Phe Leu Thr Gly Leu Val Ala Phe Leu Glu Phe Leu Val Arg Asn Asn
                165                 170                 175

Val Leu Leu Glu Leu Leu Arg Ser Ser Leu Ile Leu Gln Gly Ser
            180                 185                 190

Trp Phe Phe Gln Ile Gly Phe Val Leu Tyr Pro Ser Gly Gly Pro
        195                 200                 205

Ala Trp Asp Leu Met Asp His Glu Asn Ile Leu Phe Leu Thr Ile Cys
        210                 215                 220

Phe Cys Trp His Tyr Ala Val Thr Ile Val Ile Val Gly Met Asn Tyr
225                 230                 235                 240

Ala Phe Ile Thr Trp Leu Val Lys Ser Arg Leu Lys Arg Leu Cys Ser
                245                 250                 255

Ser Glu Val Gly Leu Leu Lys Asn Ala Glu Arg Glu Gln Glu Ser Glu
            260                 265                 270
```

```
Glu Glu Met
        275

<210> SEQ ID NO 3
<211> LENGTH: 1332
<212> TYPE: DNA
<213> ORGANISM: Homo Sapiens
<220> FEATURE:
<221> NAME/KEY: CDS
<222> LOCATION: (1)..(825)
<223> OTHER INFORMATION:

<400> SEQUENCE: 3 atg gca aat ttc aag ggc cac gcg ctt cca ggg agt ttc ttc ctg atc      48
Met Ala Asn Phe Lys Gly His Ala Leu Pro Gly Ser Phe Phe Leu Ile
1               5                  10                  15 att ggg ctg tgt tgg tca gtg aag tac ccg ctg aag tac ttt agc cac      96
Ile Gly Leu Cys Trp Ser Val Lys Tyr Pro Leu Lys Tyr Phe Ser His
            20                  25                  30 acg cgg aag aac agc cca cta cat tac tat cag cgt ctc gag atc gtc     144
Thr Arg Lys Asn Ser Pro Leu His Tyr Tyr Gln Arg Leu Glu Ile Val
        35                  40                  45 gaa gcc gca att agg act ttg ttt tcc gtc att ggg atc ctg gca gag     192
Glu Ala Ala Ile Arg Thr Leu Phe Ser Val Ile Gly Ile Leu Ala Glu
    50                  55                  60 cag ttt gtt ccg gat ggg ccc cac ctg cac ctc tac cat gag aac cac     240
Gln Phe Val Pro Asp Gly Pro His Leu His Leu Tyr His Glu Asn His
65                  70                  75                  80 tgg ata aag tta atg aat tgg cag cac agc acc atg tac cta ttc ttt     288
Trp Ile Lys Leu Met Asn Trp Gln His Ser Thr Met Tyr Leu Phe Phe
                85                  90                  95 gca gtc tca gga att gtt gac atg ctc acc tat ctg gtc agc cac gtt     336
Ala Val Ser Gly Ile Val Asp Met Leu Thr Tyr Leu Val Ser His Val
            100                 105                 110 ccc ttg ggg gtg gac aga ctg gtt atg gct gtg gca gta ttc atg gaa     384
Pro Leu Gly Val Asp Arg Leu Val Met Ala Val Ala Val Phe Met Glu
        115                 120                 125 ggt ttc ctc ttc tac tac cac gtc cac aac cgg cct ccg ctg gac cag     432
Gly Phe Leu Phe Tyr Tyr His Val His Asn Arg Pro Pro Leu Asp Gln
    130                 135                 140 cac atc cac tca ctc ctg ctg tat gct ctg ttc gga ggg tgt gtt agt     480
His Ile His Ser Leu Leu Leu Tyr Ala Leu Phe Gly Gly Cys Val Ser
145                 150                 155                 160 atc tcc cta gag gtg atc ttc cgg gac cac att gtg ctg gaa ctt ttc     528
Ile Ser Leu Glu Val Ile Phe Arg Asp His Ile Val Leu Glu Leu Phe
                165                 170                 175 cga acc agt ctc atc att ctt cag gga acc tgg ttc tgg cag att ggg     576
Arg Thr Ser Leu Ile Ile Leu Gln Gly Thr Trp Phe Trp Gln Ile Gly
            180                 185                 190 ttt gtg ctg ttc cca cct ttt gga aca ccc gaa tgg gac cag aag gat     624
Phe Val Leu Phe Pro Pro Phe Gly Thr Pro Glu Trp Asp Gln Lys Asp
        195                 200                 205 gat gcc aac ctc atg ttc atc acc atg tgc ttc tgc tgg cac tac ctg     672
Asp Ala Asn Leu Met Phe Ile Thr Met Cys Phe Cys Trp His Tyr Leu
    210                 215                 220 gct gcc ctc agc att gtg gcc gtc aac tat tct ctt gtt tac tgc ctt     720
Ala Ala Leu Ser Ile Val Ala Val Asn Tyr Ser Leu Val Tyr Cys Leu
225                 230                 235                 240 ttg act cgg atg aag aga cac gga agg gga gaa atc att gga att cag     768
Leu Thr Arg Met Lys Arg His Gly Arg Gly Glu Ile Ile Gly Ile Gln
                245                 250                 255
```

```
aag ctg aat tca gat gac act tac cag acc gcc ctc ttg agt ggc tca    816
Lys Leu Asn Ser Asp Asp Thr Tyr Gln Thr Ala Leu Leu Ser Gly Ser
        260                 265                 270 gat gag gaa tgagccgaga tgcggagggc gcagatgtcc cactgcacag             865
Asp Glu Glu
        275 ctggaatgaa tggagttcat cccctccacc tgaatgcctg ctgtggtctg atcttaaggg    925 tctatatatt tgcacctcct cattcaacac agggctggag gttctacaac aggaaatcag    985 gcctacagca tcctgtgtat cttgcagttg ggattttttaa acatactata aagtctgtgt   1045 tggtatagta cccttcataa ggaaaaatga agtaatgcct ataagtagca ggcctttgtg   1105 cctcagtgtc aagagaaatc aagagatgct aaaagcttta caatggaagt ggcctcatgg   1165 atgaatccgg ggtatgagcc caggagaacg tgctgctttt ggtaacttat ccctttttct   1225 cttaagaaag caggtacttt cttattagaa atatgttaga atgtgtaagc aaacgacagt   1285 gcctttagaa ttacaattct aacttacata tttttttgaaa gtaaaat                 1332
```

<210> SEQ ID NO 4
<211> LENGTH: 275
<212> TYPE: PRT
<213> ORGANISM: Homo Sapiens

<400> SEQUENCE: 4

```
Met Ala Asn Phe Lys Gly His Ala Leu Pro Gly Ser Phe Phe Leu Ile
1               5                   10                  15

Ile Gly Leu Cys Trp Ser Val Lys Tyr Pro Leu Lys Tyr Phe Ser His
            20                  25                  30

Thr Arg Lys Asn Ser Pro Leu His Tyr Tyr Gln Arg Leu Glu Ile Val
        35                  40                  45

Glu Ala Ala Ile Arg Thr Leu Phe Ser Val Ile Gly Ile Leu Ala Glu
    50                  55                  60

Gln Phe Val Pro Asp Gly Pro His Leu His Leu Tyr His Glu Asn His
65                  70                  75                  80

Trp Ile Lys Leu Met Asn Trp Gln His Ser Thr Met Tyr Leu Phe Phe
                85                  90                  95

Ala Val Ser Gly Ile Val Asp Met Leu Thr Tyr Leu Val Ser His Val
            100                 105                 110

Pro Leu Gly Val Asp Arg Leu Val Met Ala Val Ala Val Phe Met Glu
        115                 120                 125

Gly Phe Leu Phe Tyr Tyr His Val His Asn Arg Pro Pro Leu Asp Gln
    130                 135                 140

His Ile His Ser Leu Leu Leu Tyr Ala Leu Phe Gly Gly Cys Val Ser
145                 150                 155                 160

Ile Ser Leu Glu Val Ile Phe Arg Asp His Ile Val Leu Glu Leu Phe
                165                 170                 175

Arg Thr Ser Leu Ile Ile Leu Gln Gly Thr Trp Phe Trp Gln Ile Gly
            180                 185                 190

Phe Val Leu Phe Pro Pro Phe Gly Thr Pro Glu Trp Asp Gln Lys Asp
        195                 200                 205

Asp Ala Asn Leu Met Phe Ile Thr Met Cys Phe Cys Trp His Tyr Leu
    210                 215                 220

Ala Ala Leu Ser Ile Val Ala Val Asn Tyr Ser Leu Val Tyr Cys Leu
225                 230                 235                 240

Leu Thr Arg Met Lys Arg His Gly Arg Gly Glu Ile Ile Gly Ile Gln
```

-continued

```
                245                 250                 255
Lys Leu Asn Ser Asp Asp Thr Tyr Gln Thr Ala Leu Leu Ser Gly Ser
        260                 265                 270

Asp Glu Glu
        275

<210> SEQ ID NO 5
<211> LENGTH: 28
<212> TYPE: DNA
<213> ORGANISM: Artificial Sequence
<220> FEATURE:
<223> OTHER INFORMATION: Oligonucleotide PCR Primer

<400> SEQUENCE: 5
ccactcaatg cgagacgtgg ccagatcc                                          28

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide PCR Primer

<400> SEQUENCE: 6
cccagtaacc ttgagcatat ctataaggc                                         29

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide PCR Primer

<400> SEQUENCE: 7
gcctccgctg gaccagcaca tc                                                22

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide PCR Primer

<400> SEQUENCE: 8
gacatctgcg ccctccgcat ctc                                               23

<210> SEQ ID NO 9
<211> LENGTH: 15
<212> TYPE: PRT
<213> ORGANISM: Homo Sapiens

<400> SEQUENCE: 9

Cys Ser Ser Glu Val Gly Leu Leu Lys Asn Ala Glu Arg Glu Gln
1               5                   10                  15
```